US008852609B2

(12) United States Patent
Weiner et al.

(10) Patent No.: US 8,852,609 B2
(45) Date of Patent: Oct. 7, 2014

(54) CONSENSUS SEQUENCES OF CHIKUNGUNYA VIRAL PROTEINS, NUCLEIC ACID MOLECULES ENCODING THE SAME, AND COMPOSITIONS AND METHODS FOR USING THE SAME

(75) Inventors: David B. Weiner, Merion, PA (US); Karuppiah Muthumani, Cherry Hill, NJ (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 646 days.

(21) Appl. No.: 12/936,186

(22) PCT Filed: Apr. 6, 2009

(86) PCT No.: PCT/US2009/039656
§ 371 (c)(1), (2), (4) Date: Jan. 11, 2011

(87) PCT Pub. No.: WO2009/124312
PCT Pub. Date: Oct. 8, 2009

(65) Prior Publication Data
US 2011/0104198 A1    May 5, 2011

Related U.S. Application Data

(60) Provisional application No. 61/042,661, filed on Apr. 4, 2008.

(51) Int. Cl.
| | |
|---|---|
| *A61K 39/12* | (2006.01) |
| *C07H 21/04* | (2006.01) |
| *C07K 14/005* | (2006.01) |
| *C12N 7/00* | (2006.01) |
| *A61K 39/00* | (2006.01) |
| *A61K 39/39* | (2006.01) |

(52) U.S. Cl.
CPC ..... *C07K 14/005* (2013.01); *A61K 2039/55522* (2013.01); *A61K 2039/575* (2013.01); *A61K 2039/55516* (2013.01); *A61K 39/39* (2013.01); *A61K 2039/55588* (2013.01); *C07H 21/04* (2013.01); *A61K 39/12* (2013.01); *A61K 2039/53* (2013.01); *C12N 7/00* (2013.01); *C12N 2770/36121* (2013.01); *C12N 2770/36122* (2013.01)
USPC .................................. 424/218.1; 536/23.72

(58) Field of Classification Search
None
See application file for complete search history.

(56) References Cited

U.S. PATENT DOCUMENTS

| | | |
|---|---|---|
| 4,722,848 A | 2/1988 | Paoletti et al. |
| 4,945,050 A | 7/1990 | Sanford et al. |

(Continued)

FOREIGN PATENT DOCUMENTS

| | | |
|---|---|---|
| JP | 2004-510440 | 4/2004 |
| WO | WO 2007/105111 | * 9/2007 |

(Continued)

OTHER PUBLICATIONS

Drexler et al., Current Opinion in Biotechnology, 2004, 15:506-512.*

(Continued)

*Primary Examiner* — Nicole Kinsey White
(74) *Attorney, Agent, or Firm* — Pepper Hamilton LLP

(57) ABSTRACT

Consensus CHIKV E1 protein, consensus CHIKV E2 protein, consensus CHIKV capsid protein, or fragments and homologues thereof, and nucleic acid molecules that encode the same are disclosed. A consensus CHIKV Env protein which includes CHIKV E1 consensus protein, CHIKV E2 consensus protein, CHIKV E3 consensus protein, or fragments and homologues thereof and nucleic acid molecules that encode the same are also disclosed. Compositions and recombinant vaccines comprising CHIKV consensus proteins, and methods of using them are disclosed.

20 Claims, 7 Drawing Sheets

(56) References Cited

U.S. PATENT DOCUMENTS

| | | | |
|---|---|---|---|
| 5,017,487 | A | 5/1991 | Stunnenberg et al. |
| 5,036,006 | A | 7/1991 | Sanford et al. |
| 5,077,044 | A | 12/1991 | Stocker |
| 5,110,587 | A | 5/1992 | Paoletti et al. |
| 5,112,749 | A | 5/1992 | Brey, III et al. |
| 5,174,993 | A | 12/1992 | Paoletti |
| 5,223,424 | A | 6/1993 | Cochran et al. |
| 5,225,336 | A | 7/1993 | Paoletti |
| 5,240,703 | A | 8/1993 | Cochran |
| 5,242,829 | A | 9/1993 | Panicali et al. |
| 5,273,525 | A | 12/1993 | Hofmann |
| 5,294,441 | A | 3/1994 | Curtiss, III |
| 5,294,548 | A | 3/1994 | McLinden et al. |
| 5,310,668 | A | 5/1994 | Ellis et al. |
| 5,387,744 | A | 2/1995 | Curtiss, III et al. |
| 5,389,368 | A | 2/1995 | Curtiss, III |
| 5,424,065 | A | 6/1995 | Curtiss, III et al. |
| 5,439,440 | A | 8/1995 | Hofmann |
| 5,451,499 | A | 9/1995 | Cochran |
| 5,453,364 | A | 9/1995 | Paoletti |
| 5,462,734 | A | 10/1995 | Letchworth, III et al. |
| 5,470,734 | A | 11/1995 | Sondermeijer et al. |
| 5,482,713 | A | 1/1996 | Paoletti |
| 5,580,859 | A | 12/1996 | Felgner et al. |
| 5,593,972 | A | 1/1997 | Weiner et al. |
| 5,676,594 | A | 10/1997 | Joosten |
| 5,702,359 | A | 12/1997 | Hofmann et al. |
| 5,703,055 | A | 12/1997 | Felgner et al. |
| 5,739,118 | A | 4/1998 | Carrano et al. |
| 5,810,762 | A | 9/1998 | Hofmann |
| 5,817,637 | A | 10/1998 | Weiner et al. |
| 5,830,876 | A | 11/1998 | Weiner et al. |
| 5,962,428 | A | 10/1999 | Carrano et al. |
| 5,981,505 | A | 11/1999 | Weiner et al. |
| 5,993,434 | A | 11/1999 | Dev et al. |
| 6,014,584 | A | 1/2000 | Hofmann et al. |
| 6,055,453 | A | 4/2000 | Hofmann et al. |
| 6,068,650 | A | 5/2000 | Hofmann et al. |
| 6,110,161 | A | 8/2000 | Mathiesen |
| 6,120,493 | A | 9/2000 | Hofmann |
| 6,135,990 | A | 10/2000 | Heller et al. |
| 6,181,964 | B1 | 1/2001 | Hoffmann et al. |
| 6,216,034 | B1 | 4/2001 | Hoffmann et al. |
| 6,233,482 | B1 | 5/2001 | Hoffmann et al. |
| 6,241,701 | B1 | 6/2001 | Hoffmann |
| 6,347,247 | B1 | 2/2002 | Dev et al. |
| 6,418,341 | B1 | 7/2002 | Hoffmann et al. |
| 6,451,002 | B1 | 9/2002 | Dev et al. |
| 6,516,223 | B2 | 2/2003 | Hofmann |
| 6,567,694 | B2 | 5/2003 | Hayakawa |
| 6,569,149 | B2 | 5/2003 | Dev et al. |
| 6,610,044 | B2 | 8/2003 | Mathiesen |
| 6,654,636 | B1 | 11/2003 | Dev et al. |
| 6,678,556 | B1 | 1/2004 | Nolan et al. |
| 6,697,669 | B2 | 2/2004 | Dev et al. |
| 6,763,264 | B2 | 7/2004 | Hoffman |
| 6,778,853 | B1 | 8/2004 | Heller et al. |
| 6,865,416 | B2 | 3/2005 | Dev et al. |
| 7,078,218 | B2 | 7/2006 | Smith et al. |
| 7,245,963 | B2 | 7/2007 | Draghia-Akli et al. |
| 2005/0052630 | A1 | 3/2005 | Smith et al. |
| 2007/0041941 | A1 | 2/2007 | Weiner et al. |
| 2007/0104686 | A1 | 5/2007 | Weiner et al. |
| 2008/0091135 | A1 | 4/2008 | Draghia-Akli |

FOREIGN PATENT DOCUMENTS

| | | |
|---|---|---|
| WO | WO2007105111 | 9/2007 |
| WO | 2008026225 | 3/2008 |
| WO | 2010062396 | 6/2010 |

OTHER PUBLICATIONS

Kumar et al., DNA and Cell Biology, 2006, 25(7):383-392.*

Robinson, M.C., "An epidemic of virus disease in Southern Province, Tanganyika Territory, in 1952-53", I. Clinical features. Trans R Soc Trop Med Hyg, 1955, 49:28-32.

Powers, A.M, et al., "Changing patterns of chikungunya virus: re-emergence of a zoonotic arbovirus", Journal of General Virology, 2007, 88:2363-2377.

Porterfield, J. H., "Antigenic characteristics and classification of the Togoviridae", The Togoviruses, 1980: 13-46.

Weaver, S.C. et al., "Transmission cycles, host range, evolution and emergence of arboviral disease", 2004, Nat. Res. Microbiol., 2004, 2:789-801.

Chevillon, C. et al., "The Chikungunya threat: an ecological and evolutionary perspective", Trends Microbiol., 2008, 16 (2):80-88.

Lahariya, C. et al., "Emergence of chikungunya virus in Indian sub-continent after 32 years: a review", J. Vector Borne Dis., 2006, 43:151-160.

Vanlandingham, D.L., "Differential infectivities of o'nyong-nyong and chikungunya virus isolates in *Anopheles* and *Aedes aegypti* mosquitoes", Am J Trop Med Hyg, 2005, 72(5): 616-21.

Yergolkar, P.N. et al., "Chikungunya outbreaks caused by African genotype, India", Emerg. Infect. Dis., 2006, 12:1580-1583.

Warner, E. et al., "Chikungunya fever diagnosed among international travelers—United States", MMWR Morb Mortal Wkly Rep, 2005-2006, 55:1040-1042.

Tsetsarkin, K.A., "A Single Mutation in Chikungunya Virus Affects Vector Specificity and Epidemic Potential", PLoS Pathog, 2007, 7;3(12):e201.

Grivard, P., "Molecular and serological diagnosis of Chikungunya virus infection", Pathol Biol, 2007, 55(10):490-494.

Vazeille, M. et al., "Two Chikungunya Isolates from the Outbreak of La Reunion (Indian Ocean) Exhibit Different Patterns of Infection in the Mosquito, *Aedes albopictus*", PLoS ONE, 2007, 11:1-9.

Hirao, L.A. et al., "Intradermal/subcutaneous immunization by electrophoration improves plasmid vaccine delivery and potency in pigs and *Rhesus macaques*", Vaccine, 2008, 17;26(3):440-448.

Feng, G.H. et al., "Immunologic analysis induced by DNA vaccine encoding E protein of Beijing-1 strain derived from Japanese encephalitis virus", Intervirology, 2007, 50(2):93-98.

Fallacara, F. et al., "Chikungunya virus strain ITA07-RA1, complete genome", XP000002657425, 2007, Database accession No. EU244823.

Arankalle, V.A. et al., "Chikungunya virus strain IND-00-MH4, complete genome", XP000002657426, 2007, Database accession No. EF027139.

Parola, P. et al., "Chikungunya virus strain LR2006_OPY1, complete genome", XP000002657427, 2006, Database accession No. DQ443544.

Kowalzik, S. et al, "Chikungunya virus Wuerzburg 1, complete genome", XP000002657428, 2007, Database accession No. EU037962.

Muthumani, K. et al., "Immunogenicity of novel consensus-based DNA vaccines against Chikungunya virus", 2008, Vaccine, 26(40):5128-5134.

Mallilankaraman, K. et al., "A DNA vaccine against Chikungunya virus is protective in mice and induces neutralizing antibodies in mice and nonhuman primates", 2011, 5(1):1-13.

* cited by examiner

Figure 1
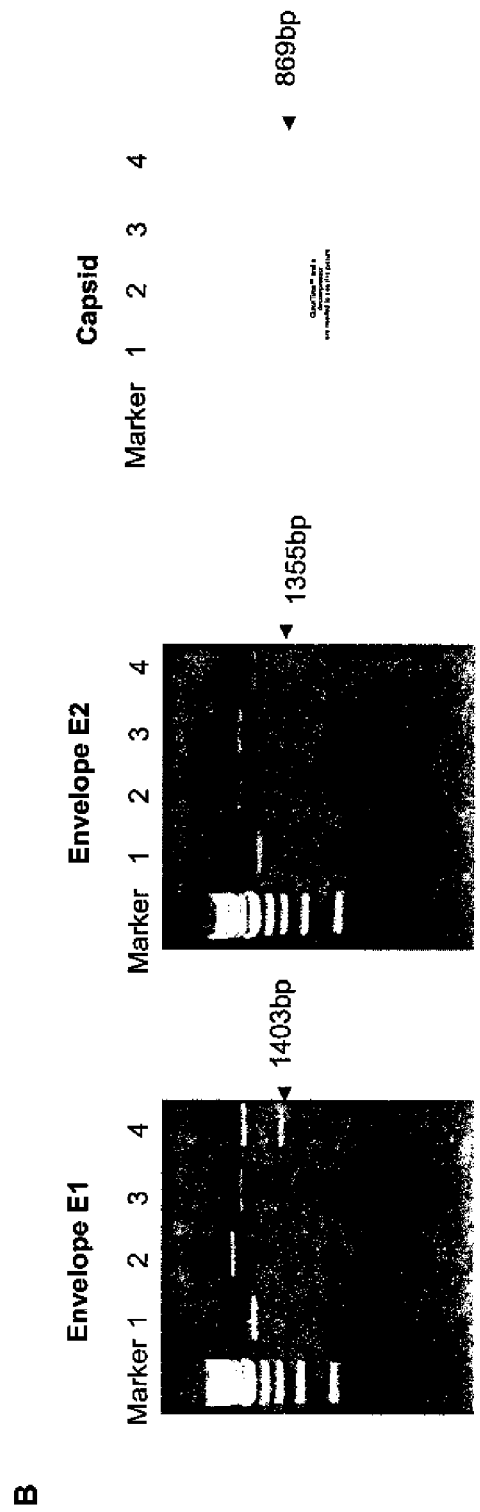

Figure 2
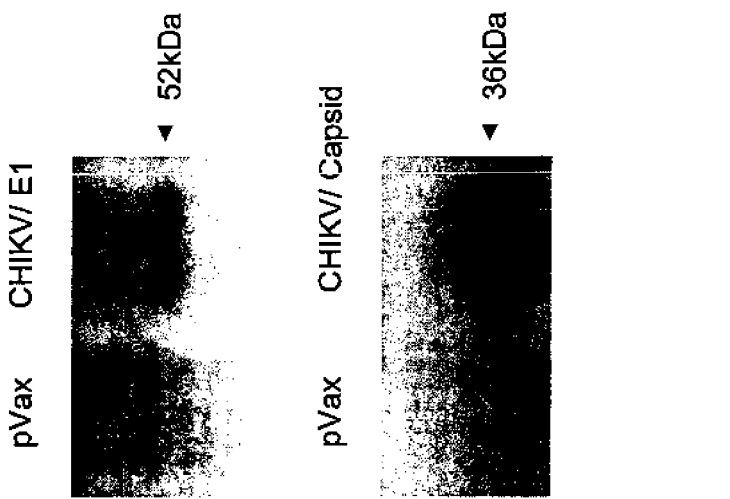
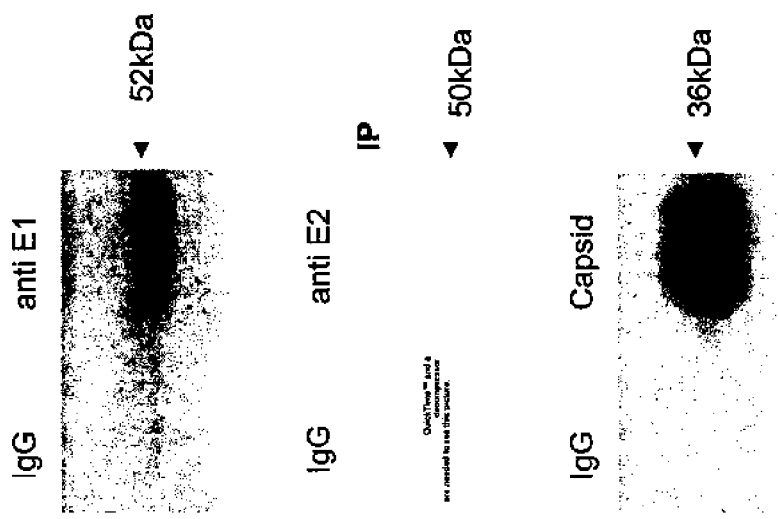

Figure 5
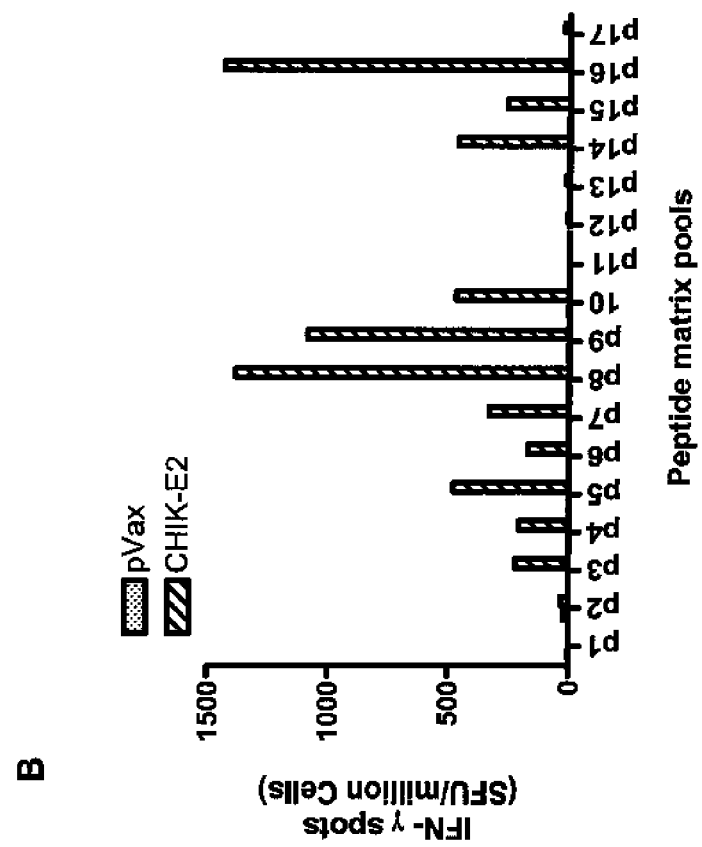
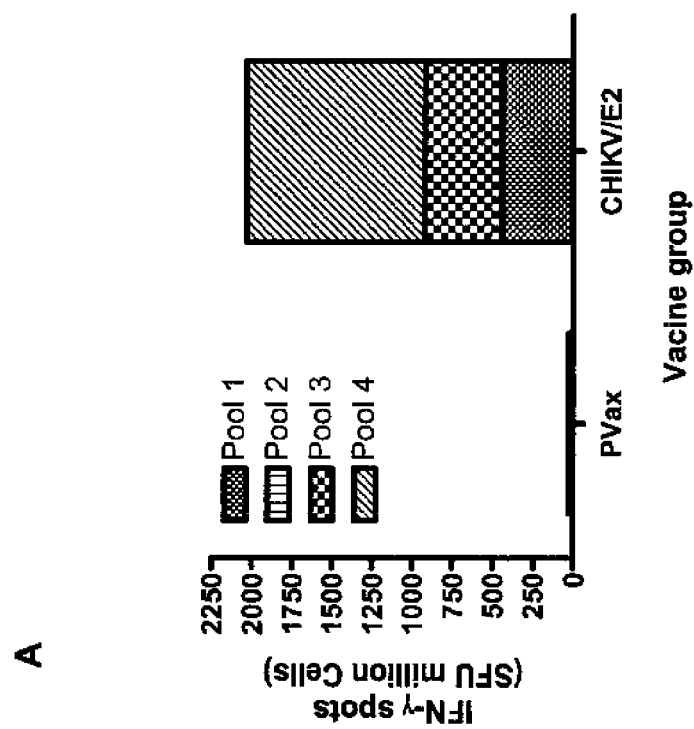

CONSENSUS SEQUENCES OF CHIKUNGUNYA VIRAL PROTEINS, NUCLEIC ACID MOLECULES ENCODING THE SAME, AND COMPOSITIONS AND METHODS FOR USING THE SAME

CROSS-REFERENCE TO RELATED APPLICATIONS

This application is the U.S. National Stage filing of and claims priority to International Application Serial No. PCT/US2009/039656 filed Apr. 6, 2009, which claims priority to U.S. Provisional Patent Application No. 61/042,661, filed Apr. 4, 2008, each of which is incorporated herein by reference in its entirety.

FIELD OF THE INVENTION

The present invention relates to vaccines and methods for prophylactically and/or therapeutically immunizing individuals against Chickungunya Viruses.

BACKGROUND OF THE INVENTION

Immunotherapy refers to modulating a person's immune responses to impart a desirable therapeutic effect. Immunotherapeutics refer to those compositions which, when administered to an individual, modulate the individual's immune system sufficient to ultimately decrease symptoms which are associated with undesirable immune responses or to ultimately alleviate symptoms by increasing desirable immune responses. In some cases, immunotherapy is part of a vaccination protocol in which the individual is administered a vaccine that exposes the individual to an immunogen against which the individual generates an immune response in such cases, the immunotherapeutic increases the immune response and/or selectively enhances a portion of the immune response (such as the cellular arm or the humoral arm) which is desirable to treat or prevent the particular condition, infection or disease.

Vaccine protocols can be improved by the delivery of agents that modulate a person's immune responses to induce an improved immune response. In some vaccination protocols in which the individual is administered a vaccine that exposes the individual to an immunogen against which the individual generates an immune response, an agent is provided that increases the immune response and/or selectively enhances a portion of the immune response (such as the cellular arm or the humoral arm) which is desirable to treat or prevent the particular condition, infection or disease.

Vaccines are useful to immunize individuals against target antigens such as allergens, pathogen antigens or antigens associated with cells involved in human diseases. Antigens associated with cells involved in human diseases include cancer-associated tumor antigens and antigens associated with cells involved in autoimmune diseases.

In designing such vaccines, it has been recognized that vaccines that produce the target antigen in cells of the vaccinated individual are effective in inducing the cellular arm of the immune system. Specifically, live attenuated vaccines, recombinant vaccines which use avirulent vectors, and DNA vaccines each lead to the production of antigens in the cell of the vaccinated individual which results in induction of the cellular arm of the immune system. On the other hand, killed or inactivated vaccines, and sub-unit vaccines which comprise only proteins do not induce good cellular immune responses although they do induce an effective humoral response.

A cellular immune response is often necessary to provide protection against pathogen infection and to provide effective immune-mediated therapy for treatment of pathogen infection, cancer or autoimmune diseases. Accordingly, vaccines that produce the target antigen in cells of the vaccinated individual such as live attenuated vaccines, recombinant vaccines that use avirulent vectors and DNA vaccines are often preferred.

Chikungunya virus (CHIKV) is an alphavirus indigenous to tropical Africa and Asia, where it is transmitted to humans by the bite of infected mosquitoes, usually of the genus *Aedes* [1]. Chikungunya fever, the disease caused by CHIKV, was first recognized in epidemic form in East Africa during 1952-1953 [2]. Infection of humans by CHIKV can cause a syndrome characterized by fever, headache, rash, malaise, nausea, vomiting, myalgia, severe arthralgia and occasionally neurological manifestations such as acute limb weakness. It is also associated with a fatal haemorrhagic condition. Other symptoms include muscle aches and retro-orbital pains. Chikungunya disease is rarely fatal but is associated with significant morbidity. Chikungunya illness has an approximate incubation period of 1-2 weeks. The word "chikungunya" is thought to derive from description in local dialect of the contorted posture of patients afflicted with the severe joint pain associated with this disease [1-3].

Because Chikungunya has epidemic potential that can produce a sudden debilitating disease, it is a potential threat to the developing world, the developed world based on its continued spread and as military threat due to soldier deployment in newly emerging endemic region conflict zones is considerable. CHIKV infections have a significant impact economically as, local businesses are affected by absenteeism in endemic areas due to the incapacitating symptoms of this infection on employees. This economic effect is highest on the individual family members who are unable to work for weeks or months. Due to the debilitating infection sequelai, the lack of specific antiviral treatment and any current usable vaccine to prevent the disease is a major impediment to managing or controlling new CHIKV outbreaks.

CHIKV is spread by the bite of an infected mosquito. Mosquitoes become infected when they feed on CHIKV infected individuals. Monkeys, and possibly other wild animals, may also get infected but their role as reservoirs of the CHIKV is not yet documented. Infected mosquitoes can then spread the virus to other humans when they bite. *Aedes aegypti* (the yellow fever mosquito), a household container breeder and aggressive daytime biter which is attracted to humans, is the primary vector of CHIKV to humans. *Aedes albopictus* (the Asian tiger mosquito) may also play a role in human transmission is Asia, and various forest-dwelling mosquito species in Africa have been found to be infected with the virus [11-17]. Because CHIK fever epidemics are sustained by human-mosquito-human transmission, the epidemic cycle is similar to those of dengue and urban yellow fever. Large outbreaks of CHIK fever have been reported recently on several islands in the Indian Ocean and in India [4-7].

Since late 2004, the Chikungunya virus has reemerged with large outbreaks in various parts of the world predominantly in the Indian Ocean islands. At the beginning of 2006, after a period of lower transmission during the winter and with the arrival of the Southern Hemisphere summer, Reunion Island suffered an explosive outbreak. An estimate of 266,000 residents (population 770,000) infected with CHIKV was reported, and 248 death certificates gave CHIKV as the possible cause of death [10,12]. Evidence for intrauterine infection in pregnant women and vertical transmission has been documented [12, 13, 17]. Sequence analysis has revealed the existence of geographically clustered lineages of the virus. Phylogenetic analyses based on partial E1 sequences revealed the existence of three distinct phylogroups for CHIKV: one with the West African isolates, another including the Asian isolates and one regrouping the Eastern, Central and South African isolates [15,17].

In 2006, CHIK fever cases also have been reported in travelers returning from known outbreak areas to Europe, Canada, the Caribbean (Martinique), and South America (French Guyana) [5-9]. During 2005-2006, 12 cases of CHIK fever were diagnosed serologically and virologically at CDC (USA) in travelers who arrived in the United States from areas known to be epidemic or endemic for CHIK fever [10].

These infections have caused public health crises and grabbed the attention of the researchers worldwide. Importantly, most Chikungunya virus infections completely resolve within weeks or months. There have been, however, documented cases of CHIKV-induced arthralgia persisting for several years developing chronic joint problems. The fact that infection resolves after a long period supports that the immune system can rally to control this infection eventually. Furthermore, such a clearance phenotype supports a role in clearance for the T cell response. Earlier attempts to develop vaccines against Chikungunya such as formalin killed vaccine, Tween ether inactivated virus vaccine and live attenuated vaccines were moderately successful however, they were discontinued for various reasons [3]. Moreover all these vaccines were reported to produce only a serological response without induction of useful cellular immunity.

The frequency of recent epidemics in the Indian Ocean and La Reunion islands suggests that a new vector perhaps is carrying the virus, as *Aedes aegypti* are not found there. In fact, a relative the Asian tiger mosquito, *Aedes albopictus*, may be the culprit which and has raised concerns in the world health community regarding the potential for a CHIK virus pandemic.

Accordingly steps should be taken to develop methods for control of CHIKV. Unfortunately, currently is no specific treatment for Chikungunya virus and there is no vaccine currently available. Recently studies have demonstrated that an envelope E1-A226V mutation is directly responsible for a significant increase in CHIKV infectivity for *Aedes albopictus*, and further confirmed that a single amino acid substitution can influence vector specificity. This finding provides a plausible explanation of how this mutant virus caused an epidemic in a region lacking the typical insect vector [18]. There is no specific vaccine or specific antiviral treatment for Chikungunya. Live attenuated vaccine trials were carried out in 2000, but funding for the project was discontinued and there is no vaccine currently available. However, several adverse events associated with this prior vaccine are well documented, accordingly, new vaccine strategies must be developed [3,5].

The sheer magnitude of the 2005-2007, Chikungunya outbreaks underscores the need for a safe and effective vaccine against CHIKV [6]. There remains a need for a vaccine which can prevent individuals from becoming infected with CHIKV infection. There remains a need for treatments that are effective to treat individuals who have CHIKV infection.

SUMMARY OF THE INVENTION

The present invention relates to a composition comprising an isolated nucleic acid molecule that encodes a consensus sequence for CHIKV protein E1 or immunogenic consensus fragments thereof.

The present invention relates to a comprising composition an isolated nucleic acid molecule that encodes a consensus sequence for CHIKV protein E2 or immunogenic fragments thereof.

The present invention relates to a composition comprising an isolated nucleic acid molecule that encodes a consensus sequence for CHIKV protein capsid or immunogenic consensus fragments thereof.

The present invention relates to a composition comprising an isolated nucleic acid molecule that encodes a chimeric gene comprising consensus sequences for CHIKV protein E1, CHIKV protein E2 and CHIKV protein E3, or homologous sequences thereof or immunogenic consensus fragments or homologous sequences thereof which encode immunogenic amino acid sequences that induce immune responses against each of CHIKV protein E1, CHIKV protein E2 and CHIKV protein E3.

The present invention relates to injectable pharmaceutical compositions comprising an isolated nucleic acid molecule that encodes a consensus sequence for CHIKV protein E1 or immunogenic consensus fragments thereof.

The present invention relates to injectable pharmaceutical compositions comprising an isolated nucleic acid molecule that encodes a consensus sequence for CHIKV protein E2 or immunogenic consensus fragments thereof.

The present invention relates to injectable pharmaceutical compositions comprising an isolated nucleic acid molecule that encodes a consensus sequence for CHIKV protein capsid or immunogenic consensus fragments thereof.

The present invention relates to injectable pharmaceutical compositions comprising an isolated nucleic acid molecule that encodes a chimeric gene comprising consensus sequences for CHIKV protein E1, CHIKV protein E2 and CHIKV protein E3, or homologous sequences thereof or immunogenic consensus fragments or homologous sequences thereof which encode immunogenic amino acid sequences that induce immune responses against each of CHIKV protein E1, CHIKV protein E2 and CHIKV protein E3.

The present invention further relates to methods of inducing an immune response in an individual against CHIKV, comprising administering to the individual a composition an isolated nucleic acid molecule that encodes a consensus sequence for CHIKV protein E1 or immunogenic consensus fragments thereof.

The present invention further relates to methods of inducing an immune response in an individual against CHIKV, comprising administering to the individual a composition an isolated nucleic acid molecule that encodes a consensus sequence for CHIKV protein E2 or immunogenic consensus fragments thereof.

The present invention further relates to methods of inducing an immune response in an individual against CHIKV, comprising administering to the individual a composition an isolated nucleic acid molecule that encodes a consensus sequence for CHIKV protein capsid or immunogenic consensus fragments thereof.

The present invention further relates to methods of inducing an immune response in an individual against CHIKV, comprising administering to the individual a composition an isolated nucleic acid molecule that encodes a consensus sequences for CHIKV protein E1, CHIKV protein E2 and CHIKV protein E3, or homologous sequences thereof or immunogenic consensus fragments or homologous sequences thereof which encode immunogenic amino acid sequences that induce immune responses against each of CHIKV protein E1, CHIKV protein E2 and CHIKV protein E3.

The present invention further relates to recombinant vaccines comprising a nucleotide sequence that encodes a consensus sequence for CHIKV protein capsid, CHIKV protein E1, CHIKV protein E2, or immunogenic consensus fragments thereof or an isolated nucleic acid molecule that encodes a consensus sequences for CHIKV protein E1, CHIKV protein E2 and CHIKV protein E3, or homologous sequences thereof or immunogenic consensus fragments or homologous sequences thereof which encode immunogenic amino acid sequences that induce immune responses against each of CHIKV protein E1, CHIKV protein E2 and CHIKV protein E3, and to methods of inducing an immune response in an individual against CHIKV comprising administering such a recombinant vaccine to an individual.

BRIEF DESCRIPTION OF THE FIGURES

FIG. 1: (A) Schematic representation of the strategy for cloning the IgE-leader CHIKV fusion gene into the pVax1 vector. (B) Agarose gel photograph showing the CHIKV plasmid (Envelope E1, E2 and Capsid) linear specific band indicated (lane 4) with Kpn1 and Not1 double digestion which produced the size of 1403 bp, 1355 bp and 869 bp size, respectively.

FIG. 2: Characterization of CHIKV constructs. (A) Shows $S^{35}$-labeled in vitro translation of the synthesized construct. The antigens CHIKV-E1, CHIKV-E2 and CHIKV-Capsid were translated and was immunoprecipitated using the specific E1, E2 and Caspsid antibodies respectively and run on a 12% SDS gel, and subject to radiographic analysis. The antigen runs at its predicted molecular weight, confirming expression. (B) Western blot analysis of CHIKV-E1 and CHIKV-Capsid construct in BHK-21 cells. Two days post transfection, the transfected cell lysates were prepared and immunoblot with polyclonal CHIKV-E1 antiserum, which was raised in mice shows the expression of 52 kDa E1 protein and 36 kDa for Capsid protein.

FIG. 5: Interferon-γ response to CHIKV envelope E2 measured by ELISpot. C57BL/6 mice were immunized two times, each 2 weeks apart, with 25 μg pVax1 vector or pCHIKV-E2 and sacrificed 1 week later. (A) Splenocytes were harvested and cultured overnight in the presence of R10 (negative control) or 10 μg/ml of one of four peptide pools, made up of 15-mer peptides overlapping by 9 amino acids, spanning the length of the E2 protein. Responses to CHIKV-E2 are shown as stacked group mean responses. (B) Splenocytes were harvested and cultured overnight in the presence of R10 (negative control) or 10 μg/ml of one of eighteen peptide pools, made up of 15-mer peptides overlapping by 9 amino acids, spanning the length of the matrix E2 protein. Spot forming units (SFU) were quantified by an automated ELISpot reader, and the raw values were normalized to SFU per million splenocytes. Values represent the mean of triplicate wells.

DETAILED DESCRIPTION OF PREFERRED EMBODIMENTS

Figure 3:
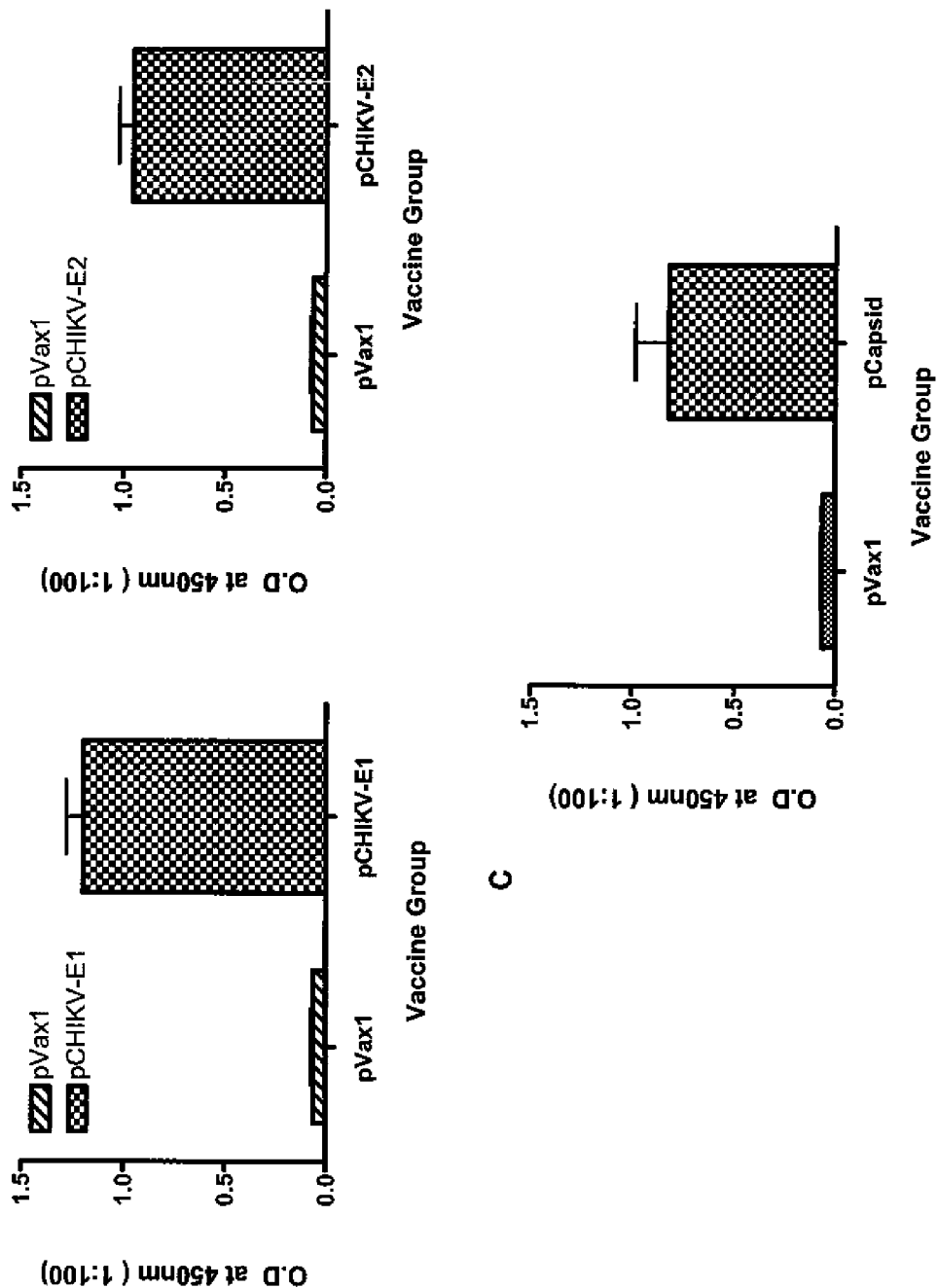
FIG. 3: Antibody ELISA. (A), (B) and (C) C57BL/6 mice were immunized two times, each 2 weeks apart, with 25 μg pVax1 vector or CHIKV plasmids as indicated and sacrificed 1 week later. Serum was collected and subject to analysis for Total IgG production against CHIKV-E1, CHIKV-E2 or CHIKV-Capsid. Serum was incubated for 1 h at 37° C. on 96-well plates coated with 2 μg/ml of respective CHIKV peptides, and antibody was detected using anti-mouse IgG-HRP. Values represent the mean (±S.D.) of duplicate wells.

As used herein, "immunonogenic consensus fragment" is meant to refer to a fragment of a consensus CHIKV protein which includes consensus sequences sufficient to impart cross-protection against two or more CHIKV strains which does not occur when a corresponding native sequence is used. Fragments are generally 10 or more amino acids in length. Some preferred lengths of CHIKV E1 are at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 105, at least 110, at least 115, at least 120, at least 125, at least 130, at least 135, at least 140, at least 145, at least 150, at least 155, at least 160, at least 165, at least 170, at least 175, at least 180, at least 185, at least 190, at least 195, at least 200, at least 205, at least 210 at least 215, at least 220, at least 225, least 230 at least 235, at least 240, at least 245, at least 250, at least 255, at least 260, at least 265, at least 270, at least 275, at least 280, at least 285, at least 290, at least 295, at least 300, at least 305, at least 310, at least 315, at least 320, at least 325, at least 330, at least 335, at least 340, at least 345, at least 350, at least 355, at least 360, at least 365, at least 370, at least 375, at least 380, at least 385, at least 390, at least 395, at least 400, at least 405, at least 410, at least 415, at least 420, at least 425, or at least 430. Some preferred lengths of CHIKV E1 are 15 or fewer, 20 or fewer, 25 or fewer, 30 or fewer, 35 or fewer, 40 or fewer, 45 or fewer, 50 or fewer, 55 or fewer, 60 or fewer, 65 or fewer, 70 or fewer, 75 or fewer, 80 or fewer, 85 or fewer, 90 or fewer, 95 or fewer, 100 or fewer, 105 or fewer, 110 or fewer, 115 or fewer, 120 or fewer, 125 or fewer, 130 or fewer, 135 or fewer, 140 or fewer, 145 or fewer, 150 or fewer, 155 or fewer, 160 or fewer, 165 or fewer, 170 or fewer, 175 or fewer, 180 or fewer, 185 or fewer, 190 or fewer, 195 or fewer, 200 or fewer, 205 or fewer, 210 or fewer, 215 or fewer, 220 or fewer, 225 or fewer, 230 or fewer, 235 or fewer, 240 or fewer, 245 or fewer, 250 or fewer, 255 or fewer, 260 or fewer, 265 or fewer, 270 or fewer, 275 or fewer, 280 or fewer, 285 or fewer, 290 or fewer, 295 or fewer, 300 or fewer, 305 or fewer, 310 or fewer, 315 or fewer, 320 or fewer, 325 or fewer, 330 or fewer, 335 or fewer, 340 or fewer, 345 or fewer, 350 or fewer, 355 or fewer, 360 or fewer, 365 or fewer, 370 or fewer, 375 or fewer, 380 or fewer, 385 or fewer, 390 or fewer, 395 or fewer, 400 or fewer, 415 or fewer, 420 or fewer, 425 or fewer, 430 or fewer, or 435 or fewer. Some preferred lengths of CHIKV E2 are at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 105, at least 110, at least 115, at least 120, at least 125, at least 130, at least 135, at least 140, at least 145, at least 150, at least 155, at least 160, at least 165, at least 170, at least 175, at least 180, at least 185, at least 190, at least 195, at least 200, at least 205, at least 210 at least 215, at least 220, at least 225, least 230 at least 235, at least 240, at least 245, at least 250, at least 255, at least 260, at least 265, at least 270, at least 275, at least 280, at least 285, at least 290, at least 295, at least 300, at least 305, at least 310, at least 315, at least 320, at least 325, at least 330, at least 335, at least 340, at least 345, at least 350, at least 355, at least 360, at least 365, at least 370, at least 375, at least 380, at least 385, at least 390, at least 395, at least 400, at least 405, at least 410, at least 415, or at least 420. Some preferred lengths of CHIKV E2 are 15 or fewer, 20 or fewer, 25 or fewer, 30 or fewer, 35 or fewer, 40 or fewer, 45 or fewer, 50 or fewer, 55 or fewer, 60 or fewer, 65 or fewer, 70 or fewer, 75 or fewer, 80 or fewer, 85 or fewer, 90 or fewer, 95 or fewer, 100 or fewer, 105 or fewer, 110 or fewer, 115 or fewer, 120 or fewer, 125 or fewer, 130 or fewer, 135 or fewer, 140 or fewer, 145 or fewer, 150 or fewer, 155 or fewer, 160 or fewer, 165 or fewer, 170 or fewer, 175 or fewer, 180 or fewer, 185 or fewer, 190 or fewer, 195 or fewer, 200 or fewer, 205 or fewer, 210 or fewer, 215 or fewer, 220 or fewer, 225 or fewer, 230 or fewer, 235 or fewer, 240 or fewer, 245 or fewer, 250 or fewer, 255 or fewer, 260 or fewer, 265 or fewer, 270 or fewer, 275 or fewer, 280 or fewer, 285 or fewer, 290 or fewer, 295 or fewer, 300 or fewer, 305 or fewer, 310 or fewer, 315 or fewer, 320 or fewer, 325 or fewer, 330 or fewer, 335 or fewer, 340 or fewer, 345 or fewer, 350 or fewer, 355 or fewer, 360 or fewer, 365 or fewer, 370 or fewer, 375 or fewer, 380 or fewer, 385 or fewer, 390 or fewer, 395 or fewer, 400 or fewer, 415 or fewer, 422 or fewer. Some preferred lengths of CHIKV capsid are at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 105, at least 110, at least 115, at least 120, at least 125, at least 130, at least 135, at least 140, at least 145, at least 150, at least 155, at least 160, at least 165, at least 170, at least 175, at least 180, at least 185, at least 190, at least 195, at least 200, at least 205, at least 210 at least 215, at least 220, at least 225, least 230 at least 235, at least 240, at least 245, at least 250 or at least 255. Some preferred lengths of CHIKV capsid are 15 or fewer, 20 or fewer, 25 or fewer, 30 or fewer, 35 or fewer, 40 or fewer, 45 or fewer, 50 or fewer, 55 or fewer, 60 or fewer, 65 or fewer, 70 or fewer, 75 or fewer, 80 or fewer, 85 or fewer, 90 or fewer, 95 or fewer, 100 or fewer, 105 or fewer, 110 or fewer, 115 or fewer, 120 or fewer, 125 or fewer, 130 or fewer, 135 or fewer, 140 or fewer, 145 or fewer, 150 or fewer, 155 or fewer, 160 or fewer, 165 or fewer, 170 or fewer, 175 or fewer, 180 or fewer, 185 or fewer, 190 or fewer, 195 or fewer, 200 or fewer, 205 or fewer, 210 or fewer, 215 or fewer, 220 or fewer, 225 or fewer, 230 or fewer, 235 or fewer, 240 or fewer, 245 or fewer, 250 or fewer, 255 or fewer or 260 or fewer. As used in the paragraph herein reference to preferred fragment sizes are intended to refer to all permutation of ranges between at least and less than such as ranges may be any number set forth as an "at least" size to any number set forth as an "less than t" size in order to provide a range of sizes such as 20-400, 20-30, 40-100, etc.

As used herein, the term "genetic construct" refers to the DNA or RNA molecules that comprise a nucleotide sequence which encodes a target protein or immunomodulating protein. The coding sequence includes initiation and termination signals operably linked to regulatory elements including a promoter and polyadenylation signal capable of directing expression in the cells of the individual to whom the nucleic acid molecule is administered.

As used herein, the term "expressible form" refers to gene constructs that contain the necessary regulatory elements operably linked to a coding sequence that encodes a target protein or an immunomodulating protein, such that when present in the cell of the individual, the coding sequence will be expressed.

As used herein, the phrase "stringent hybridization conditions" or "stringent conditions" refers to conditions under which a nucleic acid molecule will hybridize another nucleic acid molecule, but to no other sequences. Stringent conditions are sequence-dependent and will be different in different circumstances. Longer sequences hybridize specifically at higher temperatures. Generally, stringent conditions are selected to be about 5° C. lower than the thermal melting point (Tm) for the specific sequence at a defined ionic strength and pH. The Tm is the temperature (under defined ionic strength, pH and nucleic acid concentration) at which 50% of the probes complementary to the target sequence hybridize to the target sequence at equilibrium. Since the target sequences are generally present in excess, at Tm, 50% of the probes are occupied at equilibrium. Typically, stringent conditions will be those in which the salt concentration is less than about 1.0 M sodium ion, typically about 0.01 to 1.0 M sodium ion (or other salts) at pH 7.0 to 8.3 and the temperature is at least about 30° C. for short probes, primers or oligonucleotides (e.g. 10 to 50 nucleotides) and at least about 60° C. for longer probes, primers or oligonucleotides. Stringent conditions may also be achieved with the addition of destabilizing agents, such as formamide.

As used herein, "homologous" refers to the sequences homology between two nucleic acid sequences or two amino acid sequences. Two nucleic acid sequences or two amino acid sequences that are sufficiently homologous to retain immunogenic function are "homologues." Sequence homology for nucleotides and amino acids may be determined using FASTA, BLAST and Gapped BLAST (Altschul et al., Nuc. Acids Res., 1997, 25, 3389, which is incorporated herein by reference in its entirety) and PAUP* 4.0b10 software (D. L. Swofford, Sinauer Associates, Massachusetts). "Percentage of similarity" is calculated using PAUP* 4.0b10 software (D. L. Swofford, Sinauer Associates, Massachusetts). The average similarity of the consensus sequence is calculated compared to all sequences in the phylogenic tree. Briefly, the BLAST algorithm, which stands for Basic Local Alignment Search Tool is suitable for determining sequence similarity (Altschul et al., J. Mol. Biol., 1990, 215, 403410, which is incorporated herein by reference in its entirety). Software for performing BLAST analyses is publicly available though the National Center for Biotechnology Information (http://www.ncbi.nlm.nih.gov/). This algorithm involves first identifying high scoring sequence pair (HSPs) by identifying short words of length W in the query sequence that either match or satisfy some positive-valued threshold score T when aligned with a word of the same length in a database sequence. T is referred to as the neighborhood word score threshold (Altschul et al., supra). These initial neighborhood word hits act as seeds for initiating searches to find HSPs containing them. The word hits are extended in both directions along each sequence for as far as the cumulative alignment score can be increased. Extension for the word hits in each direction are halted when: 1) the cumulative alignment score falls off by the quantity X from its maximum achieved value; 2) the cumulative score goes to zero or below, due to the accumulation of one or more negative-scoring residue alignments; or 3) the end of either sequence is reached. The Blast algorithm parameters W, T and X determine the sensitivity and speed of the alignment. The Blast program uses as defaults a word length (W) of 11, the BLOSUM62 scoring matrix (see Henikoff et al., Proc. Natl. Acad. Sci. USA, 1992, 89, 10915-10919, which is incorporated herein by reference in its entirety) alignments (B) of 50, expectation (E) of 10, M=5, N=4, and a comparison of both strands. The BLAST algorithm (Karlin et al., Proc. Natl. Acad. Sci. USA, 1993, 90, 5873-5787, which is incorporated herein by reference in its entirety) and Gapped BLAST perform a statistical analysis of the similarity between two sequences. One measure of similarity provided by the BLAST algorithm is the smallest sum probability (P(N)), which provides an indication of the probability by which a match between two nucleotide sequences would occur by chance. For example, a nucleic acid is considered similar to another if the smallest sum probability in comparison of the test nucleic acid to the other nucleic acid is less than about 1, preferably less than about 0.1, more preferably less than about 0.01, and most preferably less than about 0.001.

In some embodiments, a DNA vaccine for CHIKV is provided which can be used to immunize individuals. The vaccine induces both humoral and cellular immunity in vivo.

According to some embodiments, to develop an immunogen with the ability to induce cross-reactive immune responses against Chikungunya virus (CHIKV), we designed consensus constructs against CHIKV viral envelope E1, E2 and the core protein Capsid. For these constructs 21 sequences were chosen from chikungunya viruses isolated between 1952 and 2006 that caused infection and death in humans. The DNA sequences chosen for each gene were from S27 strain (first isolate) and the strains across various countries including the La Reunion island outbreak isolates in order to avoid sampling bias. The DNA sequences were aligned and the most common nucleotide at each position was chosen for the synthetic sequence. Deduced amino acid sequences were used to guide the introduction of alignment gaps so that they were introduced between codons maintaining the reading frame. After generation of the consensus sequences, an IgE leader sequence was added to N-terminus to enhance expression and the secretion, the construct was optimized by the codon optimization, and replacement of the existing Kozak sequence with a stronger sequence (GCCGCCACC) (FIG. 1A). For analysis, a His tag was added to the C-terminus of both E1 and Capsid for expression verification. These constructs were then produced in bacterial and purified as previously described for analysis, expression and immunogenicity studies [21]. FIG. 1B depict the agrose gel electrophoresis of the constructs encoding envelope E1, E2 and Capsid DNA.

According to another embodiment, we designed a chimeric consensus construct against each of CHIKV viral envelope E1, E2 and E3. For these constructs, consensus sequences of each of E1, E2 and E3 were generated and each consensus sequences was linked to another, preferable with a sequence that encodes a protease cleavage site. In addition, an IgE leader sequence was added to N-terminus to enhance expression and the secretion.

In preferred embodiments, the constructs include the CHIKV coding sequences linked to the IgE leader sequence. However, in some embodiments, the CHIKV coding sequences is not linked to the IgE leader sequence but may, optionally, be linked a different leader sequence.

SEQ ID NO:1 refers to a nucleotide sequence that encodes consensus CHIKV-E1 protein linked to an IgE leader sequence.

SEQ ID NO:2 refers to a nucleotide sequence that encodes consensus CHIKV-E2 protein linked to an IgE leader sequence.

SEQ ID NO:3 refers to a nucleotide sequence that encodes consensus CHIKV-capsid protein linked to an IgE leader sequence.

SEQ ID NO:4 refers to a nucleotide sequence that encodes consensus CHIKV-E1 protein corresponding to SEQ ID NO:1 but without the coding sequence for the IgE leader sequence.

SEQ ID NO:5 refers to a nucleotide sequence that encodes consensus CHIKV-E2 protein corresponding to SEQ ID NO:2 but without the coding sequence for the IgE leader sequence.

SEQ ID NO:6 refers to a nucleotide sequence that encodes consensus CHIKV-capsid protein corresponding to SEQ ID NO:3 but without the coding sequence for the IgE leader sequence.

SEQ ID NO:7 refers to the amino acid sequence encoded by SEQ ID NO:1 which is the consensus CHIKV-E1 protein with the IgE leader sequence.

SEQ ID NO:8 refers to the amino acid sequence encoded by SEQ ID NO:2 which is the consensus CHIKV-E2 protein with the IgE leader sequence.

SEQ ID NO:9 refers to the amino acid sequence encoded by SEQ ID NO:3 which is the consensus CHIKV-capsid protein with the IgE leader sequence.

SEQ ID NO:10 refers to the amino acid sequence encoded by SEQ ID NO:4 which is the consensus CHIKV-E1 protein without the IgE leader sequence.

SEQ ID NO:11 refers to the amino acid sequence encoded by SEQ ID NO:5 which is the consensus CHIKV-E2 protein without the IgE leader sequence.

SEQ ID NO:12 refers to the amino acid sequence encoded by SEQ ID NO:6 which is the consensus CHIKV-capsid protein without the IgE leader sequence.

SEQ ID NO:13 refers to a nucleotide sequence that encodes consensus Env which is Kozak sequence-IgE leader sequence-CHIKV-E3 coding sequence-cleavage site-CHIKV-E2 coding sequence-cleavage site-CHIKV-E1 coding sequence-stop signal-stop signal.

SEQ ID NO:14 refers to the amino acid sequence encoded by SEQ ID NO:13 which is the consensus Env protein sequence which is IgE leader sequence-CHIKV-E3-cleavage site-CHIKV-E2-cleavage site-CHIKV-E1 coding sequence.

SEQ ID NO:15 refers to a nucleotide sequence that encodes consensus Env corresponding to SEQ ID NO:13 but without the IgE leader sequence, i.e. CHIKV-E3 coding sequence-cleavage site-CHIKV-E2 coding sequence-cleavage site-CHIKV-E1 coding sequence-stop signal-stop signal.

SEQ ID NO:16 refers to the amino acid sequence encoded by SEQ ID NO:15 which is the consensus Env protein sequence without the IgE leader sequence, i.e. CHIKV-E3-cleavage site-CHIKV-E2-cleavage site-CHIKV-E1 coding sequence.

SEQ ID NO:17 refers to the amino acid sequence of the IgE leader sequence.

The sequence GCCGCCACC refers to a preferred Kozak sequence.

When the nucleic acid molecules that encode the consensus proteins are taken up by cells of the individual the nucleotide sequences that encode the consensus proteins are expressed in the cells and the proteins are thereby delivered to the individual. Aspects of the invention provide methods of delivering the coding sequences of the consensus proteins on a plasmid; or as part of recombinant vaccines and as part of attenuated vaccines.

According to some aspects of the present invention, compositions and methods are provided which prophylactically and/or therapeutically immunize an individual against a pathogen or abnormal, disease-related cells. The vaccine may be any type of vaccine such as, a live attenuated vaccine, a recombinant vaccine or a nucleic acid or DNA vaccine.

In some embodiments, the vaccine comprises one, two or all three consensus proteins. In some embodiments, the vaccine comprises coding sequences for two consensus proteins on the same nucleic acid molecule. In some embodiments, the vaccine comprises coding sequences for two consensus proteins on two different nucleic acid molecules. In some embodiments, the vaccine comprises coding sequences for three consensus proteins on the same nucleic acid molecule. In some embodiments, the vaccine comprises coding sequences for three consensus proteins in which coding sequences for two are on the same nucleic acid molecule and coding sequences for the third are on a second nucleic acid molecule. For example, one nucleic acid molecule comprises coding sequences for E1 and E2 and the comprises coding sequences for capsid; or one nucleic acid molecule comprises coding sequences for E1 and capsid and the comprises coding sequences for E2, or one nucleic acid molecule comprises coding sequences for E2 and capsid and the comprises coding sequences for E1. In some embodiments, the vaccine comprises coding sequences for three consensus proteins in which there are three different nucleic acid molecules and each comprises a different coding sequence.

In some embodiments, the coding sequence including for consensus E1 including the IgE leader is SEQ ID NO:1. In some embodiments, the coding sequence for consensus E1 without the IgE leader is SEQ ID NO:4. In some embodiments, the consensus E1 protein with IgE leader is SEQ ID NO:7 or a fragment thereof. In some embodiments, the consensus E1 protein is SEQ ID NO:10 or a fragment thereof. In some embodiments, the consensus E1 protein with IgE leader is 80%, 90%, 95%, 98% or 99% homologous to SEQ ID NO:7. In some embodiments, the consensus E1 protein without IgE leader is 80%, 90%, 95%, 98% or 99% homologous to SEQ ID NO:10. In some embodiments, the coding sequence including for consensus E2 including the IgE leader is SEQ ID NO:2. In some embodiments, the coding sequence for consensus E2 without the IgE leader is SEQ ID NO:5. In some embodiments, the consensus E2 protein with IgE leader is SEQ ID NO:8 or a fragment thereof. In some embodiments, the consensus E2 protein is SEQ ID NO:11 or a fragment thereof. In some embodiments, the consensus E2 protein with IgE leader is 80%, 90%, 95%, 98% or 99% homologous to SEQ ID NO:7. In some embodiments, the consensus E1 protein without IgE leader is 80%, 90%, 95%, 98% or 99% homologous to SEQ ID NO:11. In some embodiments, the coding sequence including for consensus capsid including the IgE leader is SEQ ID NO:3. In some embodiments, the coding sequence for consensus E1 without the IgE leader is SEQ ID NO:6. In some embodiments, the consensus E1 protein with IgE leader is SEQ ID NO:9 or a fragment thereof. In some embodiments, the consensus E1 protein is SEQ ID NO:12 or a fragment thereof. In some embodiments, the consensus E1 protein with IgE leader is 80%, 90%, 95%, 98% or 99% homologous to SEQ ID NO:9. In some embodiments, the consensus E1 protein without IgE leader is 80%, 90%, 95%, 98% or 99% homologous to SEQ ID NO:12.

Multiple genes may be on a single nucleic acid molecule or multiple nucleic acid molecules. For example, one nucleic acid molecule comprises coding sequences for E1 and E2 and the comprises coding sequences for capsid; or one nucleic acid molecule comprises coding sequences for E1 and capsid and the comprises coding sequences for E2, or one nucleic acid molecule comprises coding sequences for E2 and capsid and the comprises coding sequences for E1. In some embodiments, the vaccine comprises coding sequences for three consensus proteins in which there are three different nucleic acid molecules and each comprises a different coding sequence. Vaccine may comprises a combination of two or more consensus sequences for E1, E2 and capsid.

In some embodiments, vaccines comprise a consensus CHIKV Env which comprises E1, E2 and E3 linked together as a single chimeric gene. In some embodiments, the individual consensus sequences are linked to eachother with sequences that encode a protease cleavage site. In some embodiments, the chimeric gene comprises fragments of each of E1, E2 and E3 such that expression of the chimeric gene in an individual results in an immune response against each of E1, E2 and E3. In some embodiments, the chimeric gene comprises SEQ ID NO:13 or a fragment thereof that comprises sufficient sequences such that expression of the protein in an individual results in an immune response against each of E1, E2 and E3. In some embodiments, the chimeric gene comprises a nucleic acid sequence that is at least 85% homologous to SEQ ID NO:13 or a fragment thereof that comprises sufficient sequences such that expression of the protein in an individual results in an immune response against each of E1, E2 and E3. In some embodiments, the chimeric gene comprises a nucleic acid sequence that is at least 90% homologous to SEQ ID NO:13 or a fragment thereof that comprises sufficient sequences such that expression of the protein in an individual results in an immune response against each of E1, E2 and E3. In some embodiments, the chimeric gene comprises a nucleic acid sequence that is at least 95% homologous to SEQ ID NO:13 or a fragment thereof that comprises sufficient sequences such that expression of the protein in an individual results in an immune response against each of E1, E2 and E3. In some embodiments, the chimeric gene comprises a nucleic acid sequence that is at least 98% homologous to SEQ ID NO:13 or a fragment thereof that comprises sufficient sequences such that expression of the protein in an individual results in an immune response against each of E1, E2 and E3. In some embodiments, the chimeric gene comprises a nucleic acid sequence that is at least 99% homologous to SEQ ID NO:13 or a fragment thereof that comprises sufficient sequences such that expression of the protein in an individual results in an immune response against each of E1, E2 and E3. In some embodiments, the chimeric gene comprises SEQ ID NO:15 or a fragment thereof that comprises sufficient sequences such that expression of the protein in an individual results in an immune response against each of E1, E2 and E3. In some embodiments, the chimeric gene comprises a nucleic acid sequence that is at least 85% homologous to SEQ ID NO:15 or a fragment thereof that comprises sufficient sequences such that expression of the protein in an individual results in an immune response against each of E1, E2 and E3. In some embodiments, the chimeric gene comprises a nucleic acid sequence that is at least 90% homologous to SEQ ID NO:15 or a fragment thereof that comprises sufficient sequences such that expression of the protein in an individual results in an immune response against each of E1, E2 and E3. In some embodiments, the chimeric gene comprises a nucleic acid sequence that is at least 95% homologous to SEQ ID NO:15 or a fragment thereof that comprises sufficient sequences such that expression of the protein in an individual results in an immune response against each of E1, E2 and E3. In some embodiments, the chimeric gene comprises a nucleic acid sequence that is at least 98% homologous to SEQ ID NO:15 or a fragment thereof that comprises sufficient sequences such that expression of the protein in an individual results in an immune response against each of E1, E2 and E3. In some embodiments, the chimeric gene comprises a nucleic acid sequence that is at least 99% homologous to SEQ ID NO:15 or a fragment thereof that comprises sufficient sequences such that expression of the protein in an individual results in an immune response against each of E1, E2 and E3.

In some embodiments, vaccines comprise a consensus CHIKV Env which encodes consensus amino acid sequences for E1, E2 and E3 linked together. In some embodiments, the individual consensus sequences are linked to each other with sequences that encode a protease cleavage site. In some embodiments, the chimeric gene encodes fragments of each of E1, E2 and E3 wherein the amino acid sequences encoded thereby are immunogenic and induce an immune response against each of E1, E2 and E3. In some embodiments, the consensus protein CHIKV Env comprises SEQ ID NO:14 or a fragment thereof that comprises sufficient sequences wherein the amino acid sequences encoded thereby are immunogenic and induce an immune response against each of E1, E2 and E3. In some embodiments, the consensus CHIKV Env protein comprises an amino acid sequence that is at least 85% homologous to SEQ ID NO:14 or a fragment thereof wherein the amino acid sequences encoded thereby are immunogenic and induce an immune response against each of E1, E2 and D. In some embodiments, the consensus CHIKV Env protein comprises an amino acid sequence that is at least 90% homologous to SEQ ID NO:14 or a fragment thereof wherein the amino acid sequences encoded thereby are immunogenic and induce an immune response against each of E1, E2 and E3. In some embodiments, the consensus CHIKV Env protein comprises an amino acid sequence that is at least 95% homologous to SEQ ID NO:14 or a fragment thereof wherein the amino acid sequences encoded thereby are immunogenic and induce an immune response against each of E1, E2 and E3. In some embodiments, the consensus CHIKV Env protein comprises an amino acid sequence that is at least 98% homologous to SEQ ID NO:14 or a fragment thereof wherein the amino acid sequences encoded thereby are immunogenic and induce an immune response against each of E1, E2 and E3. In some embodiments, the consensus CHIKV Env protein comprises an amino acid sequence that is at least 99% homologous to SEQ ID NO:14 or a fragment thereof wherein the amino acid sequences encoded thereby are immunogenic and induce an immune response against each of E1, E2 and E3. In some embodiments, the consensus CHIKV Env protein comprises an amino acid sequence that is at least 85% homologous to SEQ ID NO:16 or a fragment thereof wherein the amino acid sequences encoded thereby are immunogenic and induce an immune response against each of E1, E2 and E3. In some embodiments, the consensus CHIKV Env protein comprises an amino acid sequence that is at least 90% homologous to SEQ ID NO:16 or a fragment thereof wherein the amino acid sequences encoded thereby are immunogenic and induce an immune response against each of E1, E2 and E3. In some embodiments, the consensus CHIKV Env protein comprises an amino acid sequence that is at least 95% homologous to SEQ ID NO:16 or a fragment thereof wherein the amino acid sequences encoded thereby are immunogenic and induce an immune response against each of E1, E2 and E3. In some embodiments, the consensus CHIKV Env protein comprises an amino acid sequence that is at least 98% homologous to SEQ ID NO:16 or a fragment thereof wherein the amino acid sequences encoded thereby are immunogenic and induce an immune response against each of E1, E2 and E3. In some embodiments, the consensus CHIKV Env protein comprises an amino acid sequence that is at least 99% homologous to SEQ ID NO:14 or a fragment thereof wherein the amino acid sequences encoded thereby are immunogenic and induce an immune response against each of E1, E2 and E3.

The nucleic acid molecules may be delivered using any of several well known technologies including DNA injection (also referred to as DNA vaccination), recombinant vectors such as recombinant adenovirus, recombinant adenovirus associated virus and recombinant vaccinia virus.

DNA vaccines are described in U.S. Pat. Nos. 5,593,972, 5,739,118, 5,817,637, 5,830,876, 5,962,428, 5,981,505, 5,580,859, 5,703,055, 5,676,594, and the priority applications cited therein, which are each incorporated herein by reference. In addition to the delivery protocols described in those applications, alternative methods of delivering DNA are described in U.S. Pat. Nos. 4,945,050 and 5,036,006, which are both incorporated herein by reference.

Routes of administration include, but are not limited to, intramuscular, intransally, intraperitoneal, intradermal, subcutaneous, intravenous, intraarterially, intraoccularly and oral as well as topically, transdermally, by inhalation or suppository or to mucosal tissue such as by lavage to vaginal, rectal, urethral, buccal and sublingual tissue. Preferred routes of administration include to mucosal tissue, intramuscular, intraperitoneal, intradermal and subcutaneous injection. Genetic constructs may be administered by means including, but not limited to, traditional syringes, needleless injection devices, or "microprojectile bombardment gene guns".

Another route of administration involves the use of electroporation to deliver the genetic construct, as described in U.S. Pat. Nos. 5,273,525, 5,439,440, 5,702,359, 5,810,762, 5,993,434, 6,014,584, 6,055,453, 6,068,650, 6,110,161, 6,120,493, 6,135,990, 6,181,964, 6,216,034, 6,233,482, 6,241,701, 6,347,247, 6,418,341, 6,451,002, 6,516,223, 6,567,694, 6,569,149, 6,610,044, 6,654,636, 6,678,556, 6,697,669, 6,763,264, 6,778,853, 6,865,416, 6,939,862 and 6,958,060, which are hereby incorporated by reference.

Examples of electroporation devices and electroporation methods preferred for facilitating delivery of the DNA vaccines include those described in U.S. Pat. No. 7,245,963 by Draghia-Akli, et al., U.S. Patent Pub. 2005/0052630 submitted by Smith, et al., the contents of which are hereby incorporated by reference in their entirety. Also preferred, are electroporation devices and electroporation methods for facilitating delivery of the DNA vaccines provided in co-pending and co-owned U.S. patent application Ser. No. 11/874,072, filed Oct. 17, 2007, which claims the benefit under 35 USC 119(e) to U.S. Provisional Applications Ser.

Nos. 60/852,149, filed Oct. 17, 2006, and 60/978,982, filed Oct. 10, 2007, all of which are hereby incorporated in their entirety.

The following is an example of an embodiment using electroporation technology, and is discussed in more detail in the patent references discussed above: electroporation devices can be configured to deliver to a desired tissue of a mammal a pulse of energy producing a constant current similar to a preset current input by a user. The electroporation device comprises an electroporation component and an electrode assembly or handle assembly. The electroporation component can include and incorporate one or more of the various elements of the electroporation devices, including: controller, current waveform generator, impedance tester, waveform logger, input element, status reporting element, communication port, memory component, power source, and power switch. The electroporation component can function as one element of the electroporation devices, and the other elements are separate elements (or components) in communication with the electroporation component. In some embodiments, the electroporation component can function as more than one element of the electroporation devices, which can be in communication with still other elements of the electroporation devices separate from the electroporation component. The use of electroporation technology to deliver the vaccines is not limited by the elements of the electroporation devices existing as parts of one electromechanical or mechanical device, as the elements can function as one device or as separate elements in communication with one another. The electroporation component is capable of delivering the pulse of energy that produces the constant current in the desired tissue, and includes a feedback mechanism. The electrode assembly includes an electrode array having a plurality of electrodes in a spatial arrangement, wherein the electrode assembly receives the pulse of energy from the electroporation component and delivers same to the desired tissue through the electrodes. At least one of the plurality of electrodes is neutral during delivery of the pulse of energy and measures impedance in the desired tissue and communicates the impedance to the electroporation component. The feedback mechanism can receive the measured impedance and can adjust the pulse of energy delivered by the electroporation component to maintain the constant current.

In some embodiments, the plurality of electrodes can deliver the pulse of energy in a decentralized pattern. In some embodiments, the plurality of electrodes can deliver the pulse of energy in the decentralized pattern through the control of the electrodes under a programmed sequence, and the programmed sequence is input by a user to the electroporation component. In some embodiments, the programmed sequence comprises a plurality of pulses delivered in sequence, wherein each pulse of the plurality of pulses is delivered by at least two active electrodes with one neutral electrode that measures impedance, and wherein a subsequent pulse of the plurality of pulses is delivered by a different one of at least two active electrodes with one neutral electrode that measures impedance.

In some embodiments, the feedback mechanism is performed by either hardware or software. Preferably, the feedback mechanism is performed by an analog closed-loop circuit. Preferably, this feedback occurs every 50 µs, 20 µs, 10 µs or 1 µs, but is preferably a real-time feedback or instantaneous (i.e., substantially instantaneous as determined by available techniques for determining response time). In some embodiments, the neutral electrode measures the impedance in the desired tissue and communicates the impedance to the feedback mechanism, and the feedback mechanism responds to the impedance and adjusts the pulse of energy to maintain the constant current at a value similar to the preset current. In some embodiments, the feedback mechanism maintains the constant current continuously and instantaneously during the delivery of the pulse of energy.

When taken up by a cell, the genetic construct(s) may remain present in the cell as a functioning extrachromosomal molecule. DNA may be introduced into cells, where it is present on a transient basis, in the form of a plasmid or plasmids. Alternatively, RNA may be administered to the cell. It is also contemplated to provide the genetic construct as a linear minichromosome including a centromere, telomeres and an origin of replication. Gene constructs may constitute part of the genetic material in attenuated live microorganisms or recombinant microbial vectors which are administered to subjects. Gene constructs may be part of genomes of recombinant viral vaccines where the genetic material remains extrachromosomal. Genetic constructs include regulatory elements necessary for gene expression of a nucleic acid molecule. The elements include: a promoter, an initiation codon, a stop codon, and a polyadenylation signal. In addition, enhancers are often required for gene expression of the sequence that encodes the target protein or the immunomodulating protein. It is necessary that these elements be operably linked to the sequence that encodes the desired proteins and that the regulatory elements are operable in the individual to whom they are administered.

An initiation codon and a stop codon are generally considered to be part of a nucleotide sequence that encodes the desired protein. However, it is necessary that these elements are functional in the individual to whom the gene construct is administered. The initiation and termination codons must be in frame with the coding sequence.

Promoters and polyadenylation signals used must be functional within the cells of the individual.

Examples of promoters useful to practice the present invention, especially in the production of a genetic vaccine for humans, include but are not limited to promoters from Simian Virus 40 (SV40), Mouse Mammary Tumor Virus (MMTV) promoter, Human Immunodeficiency Virus (MV) such as the BIV Long Terminal Repeat (LTR) promoter, Moloney virus, ALV, Cytomegalovirus (CMV) such as the CMV immediate early promoter, Epstein Barr Virus (EBV), Rous Sarcoma Virus (RSV) as well as promoters from human genes such as human Actin, human Myosin, human Hemoglobin, human muscle creatine and human metalothionein.

Examples of polyadenylation signals useful to practice the present invention, especially in the production of a genetic vaccine for humans, include but are not limited to SV40 polyadenylation signals, bovine growth hormone polyadenylation (bgh-PolyA) signal and LTR polyadenylation signals. In particular, the SV40 polyadenylation signal that is in pCEP4 plasmid (Invitrogen, San Diego Calif.), referred to as the SV40 polyadenylation signal, is used.

In addition to the regulatory elements required for DNA expression, other elements may also be included in the DNA molecule. Such additional elements include enhancers. The enhancer may be selected from the group including but not limited to: human Actin, human Myosin, human Hemoglobin, human muscle creatine and viral enhancers such as those from CMV, RSV and EBV.

Genetic constructs can be provided with mammalian origin of replication in order to maintain the construct extrachromosomally and produce multiple copies of the construct in the cell. Plasmids pVAX1, pCEP4 and pREP4 from Invitrogen (San Diego, Calif.) contain the Epstein Barr virus origin of replication and nuclear antigen EBNA-1 coding region which produces high copy episomal replication without integration.

In some preferred embodiments related to immunization applications, nucleic acid molecule(s) are delivered which include nucleotide sequences that encode a consensus protein, and, additionally, genes for proteins which further enhance the immune response against such target proteins. Examples of such genes are those which encode other cytokines and lymphokines such as alpha-interferon, gamma-interferon, platelet derived growth factor (PDGF), TNF, GM-CSF, epidermal growth factor (EGF), IL-1, IL-2, 11-4, IL-6, IL-10, IL-12, IL-15, IL-28 including IL-15 having the signal sequence deleted and optionally including the signal peptide from IgE.

The compositions used in the methods may further comprise one or more of the following proteins and/or nucleic acid molecules encoding such proteins, as set forth in U.S. Ser. No. 10/139,423, which corresponds to U.S. Publication No. 20030176378, which is incorporated herein by reference: Major Histocompatibility Complex antigens including Major Histocompatibility Complex Class I antigen or Major Histocompatibility Complex Class II antigen; death domain receptors including, but not limited to, Apo-1, Fas, TNFR-1, p55, WSL-1, DR3, TRAMP, Apo-3, AIR, LARD, NGRF, DR4, DR5, KILLER, TRAIL-R2, TRICK2, and DR6; death signals, i.e. proteins that interact with the death domain receptors including, but not limited to FADD, FAP-1, TRADD, RIP, FLICE, and RAIDD; or death signals that include ligands that bind death domain receptors and initiate apoptosis including, but not limited to, FAS-L, and TNF; and mediators that interact with death domain receptors including, but not limited to, FADD, MORT1, and MyD88; toxins including proteins which kill cells such as, but not limited to, insect and snake venoms, bacterial endotoxins such as Psuedornoneus endotoxin, double chain ribosome inactivating proteins such as ricin including single chain toxin, and gelonin.

The compositions used in the methods may further comprise one or more of the following proteins and/or nucleic acid molecules encoding such proteins, as set forth in U.S. Ser. No. 10/560,650, which corresponds to U.S. Publication No. 20070041941, which is incorporated herein by reference: IL-15 including fusion proteins comprising non-IL-15 signal peptide linked to IL-15 protein sequences such as fusion proteins comprising an IgE signal peptide linked to IL-15 protein sequences, CD40L, TRAIL; TRAILrecDRC5, TRAIL-R2, TRAIL-R3, TRAIL-R4, RANK, RANK LIGAND, Ox40, Ox40 LIGAND, NKG2D, F461811 or MICA, MICB, NKG2A, NKG2B, NKG2C, NKG2E, NKG2F, CD30, CD153 (CD30L), Fos, c-jun, Sp-1, Ap1, Ap-2, p38, p65Rel, MyD88, IRAK, TRAF6, IkB, NIK, SAP K, SAP1, JNK2, JNK1B2, JNK1B1, JNK2B2, JNK2B1, JNK1A2, JNK2A1, JNK3A1, JNK3A2, NF-kappa-B2, p49 splice form, NF-kappa-B2, p100 splice form, NF-kappa-B2, p105 splice form, NF-kappa-B 50K chain precursor, NFkB p50, human IL-1.alpha., human IL-2, human IL-4, murine IL-4, human IL-5, human IL-10, human IL-15, human IL-18, human TNF-.alpha., human TNF-.beta., human interleukin 12, MadCAM-1, NGF IL-7, VEGF, TNF-R, Fas, CD40L, IL-4, CSF, G-CSF, GM-CSF, M-CSF, LFA-3, ICAM-3, ICAM-2, ICAM-1, PECAM, P150.95, Mac-1, LFA-1, CD34, RANTES, IL-8, MIP-1.alpha., E-selecton, CD2, MCP-1, L-selecton, P-selecton, FLT, Apo-1, Fas, TNFR-1, p55, WSL-1, DR3, TRAMP, Apo-3, AIR, LARD, NGRF, DR4 (TRAIL), DR5, KILLER, TRAIL-R2, TRICK2, DR6, ICE, VLA-1, and CD86 (B7.2).

The compositions used in the methods may further comprise one or more of the following proteins and/or nucleic acid molecules encoding such proteins, as set forth in U.S. Ser. No. 10/560,653, which corresponds to U.S. Publication No. 20070104686, which is incorporated herein by reference: Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, and TAP2.

An additional element may be added which serves as a target for cell destruction if it is desirable to eliminate cells receiving the genetic construct for any reason. A herpes thymidine kinase (tk) gene in an expressible form can be included in the genetic construct. The drug gangcyclovir can be administered to the individual and that drug will cause the selective killing of any cell producing tk, thus, providing the means for the selective destruction of cells with the genetic construct.

In order to maximize protein production, regulatory sequences may be selected which are well suited for gene expression in the cells the construct is administered into. Moreover, codons may be selected which are most efficiently transcribed in the cell. One having ordinary skill in the art can produce DNA constructs that are functional in the cells.

In some embodiments, gene constructs may be provided to in order to produce coding sequences for the immunomodulatory proteins described herein linked to IgE signal peptide.

One method of the present invention comprises the steps of administering nucleic acid molecules intramuscularly, intranasally, intraperatoneally, subcutaneously, intradermally, or topically or by lavage to mucosal tissue selected from the group consisting of inhalation, vaginal, rectal, urethral, buccal and sublingual.

In some embodiments, the nucleic acid molecule is delivered to the cells in conjunction with administration of a polynucleotide function enhancer or a genetic vaccine facilitator agent. Polynucleotide function enhancers are described in U.S. Pat. Nos. 5,593,972 and 5,962,428, which are each incorporated herein by reference. Genetic vaccine facilitator agents are described in U.S. Pat. No. 5,739,118, which is incorporated herein by reference. The co-agents that are administered in conjunction with nucleic acid molecules may be administered as a mixture with the nucleic acid molecule or administered separately simultaneously, before or after administration of nucleic-acid molecules. In addition, other agents which may function transfecting agents and/or replicating agents and/or inflammatory agents and which may be co-administered with a polynucleotide function enhancer include growth factors, cytokines and lymphokines such as a-interferon, gamma-interferon, GM-CSF, platelet derived growth factor (PDGF), TNF, epidermal growth factor (EGF), IL-1, IL-2, IL-4, IL-6, IL-10, IL-12 and IL-15 as well as fibroblast growth factor, surface active agents such as immune-stimulating complexes (ISCOMS), LPS analog including monophosphoryl Lipid A (WL), muramyl peptides, quinone analogs and vesicles such as squalene and squalene, and hyaluronic acid may also be used administered in conjunction with the genetic construct In some embodiments, an immunomodulating protein may be used as a polynucleotide function enhancer. In some embodiments, the nucleic acid molecule is provided in association with poly(lactide-co-glycolide) (PLG), to enhance delivery/uptake.

The pharmaceutical compositions according to the present invention comprise about 1 nanogram to about 2000 micrograms of DNA. In some preferred embodiments, pharmaceutical compositions according to the present invention comprise about 5 nanogram to about 1000 micrograms of DNA. In some preferred embodiments, the pharmaceutical compositions contain about 10 nanograms to about 800 micrograms of DNA. In some preferred embodiments, the pharmaceutical compositions contain about 0.1 to about 500 micrograms of DNA. In some preferred embodiments, the pharmaceutical compositions contain about 1 to about 350 micrograms of DNA. In some preferred embodiments, the pharmaceutical compositions contain about 25 to about 250 micrograms of DNA. In some preferred embodiments, the pharmaceutical compositions contain about 100 to about 200 microgram DNA.

The pharmaceutical compositions according to the present invention are formulated according to the mode of administration to be used. In cases where pharmaceutical compositions are injectable pharmaceutical compositions, they are sterile, pyrogen free and particulate free. An isotonic formulation is preferably used. Generally, additives for isotonicity can include sodium chloride, dextrose, mannitol, sorbitol and lactose. In some cases, isotonic solutions such as phosphate buffered saline are preferred. Stabilizers include gelatin and albumin. Iri some embodiments, a vasoconstriction agent is added to the formulation.

According to some embodiments of the invention, methods of inducing immune responses against Chikungyun virus are provided. The vaccine may be a live attenuated vaccine, a recombinant vaccine or a nucleic acid or DNA vaccine.

The nucleic acid molecule(s) may be provided as plasmid DNA, the nucleic acid molecules of recombinant vectors or as part of the genetic material provided in an attenuated vaccine. Alternatively, in some embodiments, the consensus protein may be delivered as a protein in addition to the nucleic acid molecules that encode them or instead of the nucleic acid molecules which encode them.

Genetic constructs may comprise a nucleotide sequence that encodes a target protein or an immunomodulating protein operably linked to regulatory elements needed for gene expression. According to the invention, combinations of gene constructs that include one construct that comprises an expressible form of the nucleotide sequence that encodes a target protein and one construct that includes an expressible form of the nucleotide sequence that encodes an immunomodulating protein are provided. Delivery into a living cell of the DNA or RNA molecule(s) that include the combination of gene constructs results in the expression of the DNA or RNA and production of the target protein and one or more immunomodulating proteins. An enhanced immune response against the target protein results.

In addition to using expressible forms of immunomodulating protein coding sequences to improve genetic vaccines, the present invention relates to improved attenuated live vaccines and improved vaccines that use recombinant vectors to deliver foreign genes that encode antigens. Examples of attenuated live vaccines and those using recombinant vectors to deliver foreign antigens are described in U.S. Pat. Nos. 4,722,848; 5,017,487; 5,077,044; 5,110,587; 5,112,749; 5,174,993; 5,223,424; 5,225,336; 5,240,703; 5,242,829; 5,294,441; 5,294,548; 5,310,668; 5,387,744; 5,389,368; 5,424,065; 5,451,499; 5,453,364; 5,462,734; 5,470,734; and 5,482,713, which are each incorporated herein by reference. Gene constructs are provided which include the nucleotide sequence that encodes a consensus protein or immunogenic consensus fragments thereof, wherein the nucleotide sequence is operably linked to regulatory sequences that can function in the vaccine to effect expression. The gene constructs are incorporated in the attenuated live vaccines and recombinant vaccines to produce improved vaccines according to the invention.

The present invention provides an improved method of immunizing individuals that comprises the step of delivering gene constructs to the cells of individuals as part of vaccine compositions which include DNA vaccines, attenuated live vaccines and recombinant vaccines. The gene constructs comprise a nucleotide sequence that encodes encodes a consensus protein or immunogenic consensus fragments thereof that is operably linked to regulatory sequences that can function in the vaccine to effect expression. The vaccines result in cross protection against different strains.

EXAMPLES

Example 1

Here we present data of a novel consensus-based approach to vaccine design for CHIKV, employing a DNA vaccine strategy. The vaccine cassette was designed based on CHIKV Capsid and Envelope specific consensus sequences with several modifications. The expression of Capsid, envelope E1 and E1 was evaluated using T7-coupled transcription/translation and immunoblot analysis. Adaptive constant-current electroporation technique was used to immunize C57BL/6 mice with an intramuscular injection of plasmid coding for the CHIK-Capsid, E1 and E2. Analysis of cellular immune responses, including epitope mapping, demonstrates that electroporation of these constructs induces both potent and broad cellular immunity. In addition, antibody ELISAs demonstrate that these synthetic immunogens are capable of inducing high titer antibodies capable of recognizing native antigen. Taken together, these data support further study of the use of consensus CHIK antigens in a potential vaccine cocktail.

In this study we designed a vaccine cassette based on Capsid (Cap) and Envelope (E1) and Envelope (E2) specific consensus sequences with several modifications, including codon optimization, RNA optimization, the addition of a Kozak sequence, and a substituted immunoglobulin E leader sequence. The vaccine cassette was introduced into the DNA vaccine vector pVax1 at the specific site. The vaccine constructs were checked for the inserts using specific restriction digestion and by sequencing with the primer of the T7 promoter. The final constructs were efficiently expressed based on both in vitro expression as well as using in vivo western blot analysis. This confirmed that the viral constructs were correctly expressed and processed for further immunogenicity studies.

Recently, there has been much interest in the use of EP for the delivery of DNA vaccines. Recent studies of IM immunization+EP in small animal models and non-human primates have consistently reported increases in cellular and in particular, antibody responses [20-22].

Materials and Methods

Cells and Animals:
The BHK-21 cell line obtained from the ATCC was grown and maintained in DMEM medium supplemented with 10% fetal calf serum. The mammalian plasmid expression vector, pVax1, was purchased from Invitrogen (Carlsbad, Calif.). Three- to 4-week-old female C57BL/6 mice (Jackson laboratories, Indianapolis, Ind.) were used in these experiments and divided into three experimental groups (n4). All animals were housed in a temperature-controlled, light-cycled facility in accordance with the guidelines of the National Institutes of Health (Bethesda, Md., USA) and the University of Pennsylvania (Philadelphia, Pa., USA) Institutional Animal Care and Use Committee (IACUC).

CHIKV DNA Construct and Synthesis:

The CHIKV core and envelope genes were designed by synthetic primer synthesis followed by DNA-PCR amplification using the consensus strain predicted of sequences collected from the NCBI database of all CHIKV viruses. Consensus sequences were optimized for expression, including codon and RNA optimization (GeneArt, Regensburg, Germany) and inserted into the pVax1 expression vector (Invitrogen).

In Vitro and In Vivo Expression:

Construct expression was confirmed by utilizing a T7 promoter in the pVax1 backbone and T7-based coupled transcription/translation system (Promega, Madison, Wis.) containing 535-methionine CHIKV genes. The synthesized protein was immunoprecipitated using anti-E1, anti-E2 or anti-Cap antibodies. The immunoprecipitated protein was electrophoresed on a 12% NuPage SDS-PAGE gel (Invitrogen, CA) and subsequently fixed and dried. Autoradiography was performed to detect an incorporated S35-labeled gene product. In vivo expression, BHK-21 cells ($1\times10^6$) were transfected with CHIKV constructs using Fugene transfection method (Roche, N.J.). Seventy-two hours after transfection, proteins (50 μg) were fractioned on SDS-PAGE (12%) and transferred to a PVDF membrane (Bio-Rad, Hercules, Calif.). Immunoblot analyses were performed with specific antiserum, which was raised in mice and the expressed protein s were visualized with horseradish peroxidase conjugated goat anti-mouse IgG using an ECL detection system (Amersham Pharmacia Biotech, Piscataway, N.J.) [19].

Immunization and Electrophoration

A standard protocol was used to prime animals with plasmid DNA [20]. Groups of four mice were immunized twice with pCHIKV genes (25 μg) 2-3 times, 2 weeks apart, and sacrificed 1 week following the final immunization. All immunizations were delivered into the quadriceps muscles in a total volume of 100 μl by in vivo electroporation (EP) (VGX Pharmaceuticals Inc, Blue Bell, Pa.). The animals were sacrificed 7 days after the last immunization, whereupon serum and the spleen were collected for immunology assays. Blood from both control and immunized mice was obtained 1 week after the second and third immunizations, respectively. Square-wave pulses were used in all experiments and delivered with the constant-current EKD that was designed and tested in our laboratory [20-22]. A three electrode array (3-EA) was used in the mouse experiments. The 3-EA consists of three 26-gauge solid stainless steel electrodes in an isosceles triangle formation, with the two long sides 0.5 mm in length and short side 0.3 mm in length, held together with a nonconductive plastic. Specific EP conditions for the mouse experiments were using constant current, 0.1 Amps, three pulses, 52 msec/pulse, 4 sec between pulses. The lag time between plasmid injection and EP was about 20 sec. The sequence of events for plasmid administration/EP was as follows: Place a disposable electrode assembly in the receptacle of the handle, press initiation button on handle and enter animal experimental group number, inject 50 μl of DNA construct (25 μg total DNA) plasmid using insulin syringe, immediately place needles into area surrounding the injection site, press initiation button on handle, and after 4 second countdown, pulses will be delivered. After 5 seconds following electroporation, the array is gently removed from muscle. All electrodes were completely inserted into the muscle during all treatments [21, 22]. All DNA was made using endotoxin-free Qiagen columns. All animals were housed in a temperature-controlled, light-cycled facility at the University of Pennsylvania, and their care was under the guidelines of the National Institutes of Health and the University of Pennsylvania.

Cellular Response: ELISPOT Assay

An ELISPOT assay was conducted as previously described [23]. Briefly, ELISpot 96-well plates (Millipore) were coated with anti-mouse IFN-γ capture Ab and incubated for 24 h at 4 C(R&D Systems). The following day, plates were washed and blocked for 2 h with 1% BSA. Two hundred thousand splenocytes from the immunized mice were added to each well and stimulated overnight at 37 C in 5% CO2 in the presence of RPMI 1640 (negative control), Con A (positive control), or specific peptide Ags (10 μl/ml; Invitrogen). Peptide pools consist of 15-mer peptides overlapping by 11 amino acids. After 24 h of stimulation, the cells were washed and incubated for 24 h at 4° C. with biotinylated anti-mouse IFN-γ Ab (R&D Systems). The plates were washed, and streptavidin-alkaline phosphatase (R&D Systems) was added to each well and incubated for 2 h at room temperature. The plate was washed, and 5-bromo-4-chloro-3'-indolylphosphate p-toluidine salt and nitro blue tetrazolium chloride (chromogen color reagent; R&D Systems) were added to each well. The plate was then rinsed with distilled water and dried at room temperature. Spots were counted by an automated ELISPOT reader (CTL Limited) [21-23]

Humoral Immune Response: Antibody ELISA

The antibody levels following each DNA priming injection and the humoral immune response to vaccination was determined to each CHIKV DNA constructs. Briefly, 96-well high-binding polystyrene plates (Corning, N.Y.) plates were coated overnight at 4° C. with synthesized specific peptides (2 μg/ml), which was diluted in PBS. The next day, plates were washed with PBST (PBS, 0.05% Tween 20), blocked for 1 h with 3% BSA in PBST, and incubated with 1,100 dilutions of serum from immunized and naïve mice for 1 h at 37 C. Bound IgG was detected using goat anti-mouse IgG-HRP (Research Diagnostics, NJ) at a dilution of 1:5,000. Bound enzyme was detected by the addition of the chromogen substrate solution TMB (R&D Systems), and read at 450 nm on a Biotek EL312e Bio-Kinetics reader. All serum samples were tested in duplicate [22].

Results

Consensus Construct Expression:

The expressions of the three CHIKV consensus constructs were verified using multiple techniques. To visualize the proteins produced in vitro $S^{35}$-labeled In vitro T7-coupled transcription and translation assay was performed. The translation products were immunoprecipitated using the His tag antibody and gel analysis was performed. SDS-PAGE and radiographic analysis showed that each construct (Envelope E1, E2 and Capsid) runs at its theoretically predicted molecular weight (FIG. 2A). We next sought to examine the expression of these constructs in mammalian cells vivo. Following transfection into BHK-21 cells the proteins were extracted after three days and expression was detected using specific polyclonal antibodies by Western blot analysis (FIG. 2B). In envelope E1 construct transfected cells a 52-kDa protein and a 36-kDa protein was observed in Capsid construct transfected cells upon immunoblotting with specific antibodies.

Humoral Immunogenicity

We hypothesize that the strength of our consensus immunogens to protect from lethal CHIK virus will lie with the cellular arm of the immune system. Furthermore, cross-reactive but non-neutralizing antibodies can provide a certain degree of protection against disease severity. In order to determine if our constructs induce antibody responses, we performed an antibody ELISA on CHIK-immunized mouse serum to determine antibody titer from the sera obtained after the DNA immunizations were tested for antibody response by ELISA. Anti E1 specific IgG antibody in the sera of mice immunized with envelope E1 were significantly higher than in the sera of mice immunized with vector control (FIG. 3A). Similarly anti E2 specific IgG antibody and capsid specific IgG antibody in the sera of mice immunized with envelope E2 and capsid constructs respectively were significantly higher than in the sera of mice immunized with vector control (FIGS. 3B&C). These results further supported the alternative means of plasmid delivery, specifically electroporation increased the antibody production response to the DNA vaccine immunogen.

Cellular Immunogenicity

Figure 4:
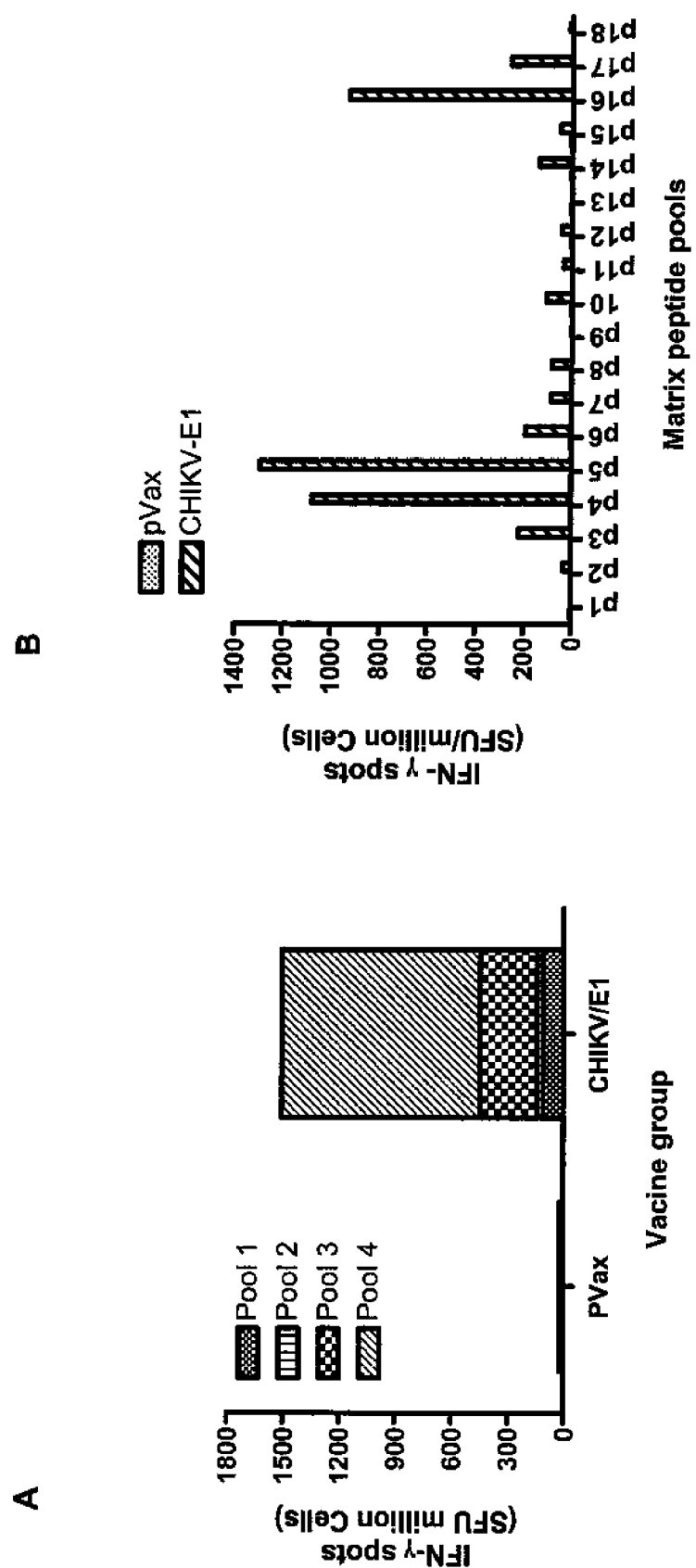
FIG. 4: Interferon-γ response to envelope E1 measured by ELISpot. C57BL/6 mice were immunized two times, each 2 weeks apart, with 25 μg pVax1 vector or pCHIKV-E1 and sacrificed 1 week later. (A) Splenocytes were harvested and cultured overnight in the presence of R10 (negative control) or 10 μg/ml of one of four peptide pools, made up of 15-mer peptides overlapping by 9 amino acids, spanning the length of the E1 protein. Responses to CHIKV-E1 are shown as stacked group mean responses. (B) Splenocytes were harvested and cultured overnight in the presence of R10 (negative control) or 10 μg/ml of one of eighteen peptide pools, made up of 15-mer peptides overlapping by 9 amino acids, spanning the length of the matrix E1 protein. Spot forming units (SFU) were quantified by an automated ELISpot reader, and the raw values were normalized to SFU per million splenocytes. Values represent the mean of triplicate wells.
Figure 6:
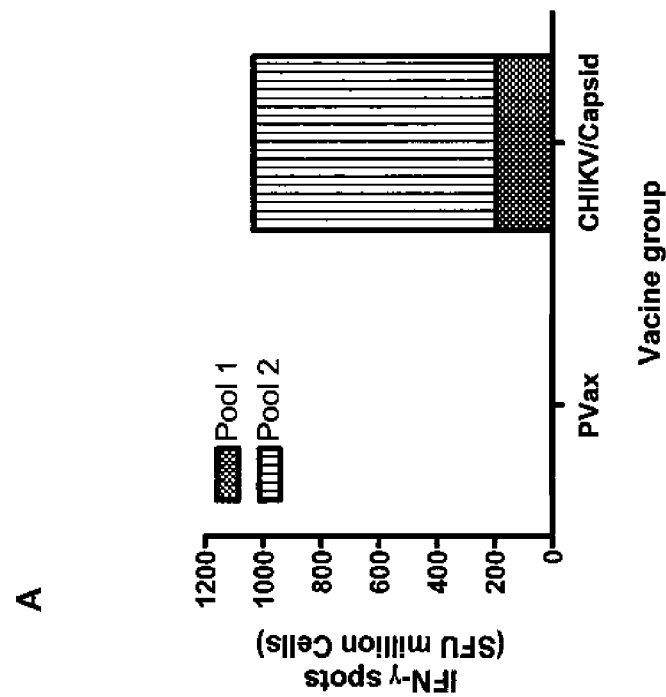
FIG. 6: Interferon-γ response CHIKV-Capsid measured by ELISpot. C57BL/6 mice were immunized two times, each 2 weeks apart, with 25 μg pVax1 vector or pCHIKV-Capsid and sacrificed 1 week later. (A) Splenocytes were harvested and cultured overnight in the presence of R10 (negative control) or 10 μg/ml of one of four peptide pools, made up of 15-mer peptides overlapping by 9 amino acids, spanning the length of the capsid protein. Responses to CHIKV-Capsid are shown as stacked group mean responses. (B) Splenocytes were harvested and cultured overnight in the presence of R10 (negative control) or 10 μg/ml of one of eighteen peptide pools, made up of 15-mer peptides overlapping by 9 amino acids, spanning the length of the matrix capsid protein. Spot forming units (SFU) were quantified by an automated ELISpot reader, and the raw values were normalized to SFU per million splenocytes. Values represent the mean of triplicate wells.

The ability of E1, E2 and Capsid constructs to induce CD8+CTL responses was determined next by IFN-γ ELISpot assays. The consensus envelope constructs E1, E2 as well as and the Capsid vaccines were able to induce strong IFN-γ responses in C57BL/6 mice after three immunizations (FIGS. 4A, 5A and 6A). For molecular characterization of the cellular immune responses induced by the envelope E1, the ELISpot assay was performed against a library of peptides spanning entire envelope E1. Seventy four 15-mer peptides with 9 amino acid overlaps between them, which span residues 1-435 of E1 protein and peptides which span 1-423 of E2 protein were used. The envelopes induced a dominant epitope HSMTNAVTI (SEQ ID NO:18) in the E1 protein (FIG. 4B) and IILYYYELY (SEQ ID NO:19) in the E2 protein (FIG. 5B). Similarly for Capsid protein, the ELIspot assay was performed against a library of peptides spanning entire Capsid protein. Forty five 15-mer peptides with 9 amino acid overlaps between them, which span residues 1-261 of Capsid protein, were used. The dominant epitope ACLVGDKVM (SEQ ID NO:20) was induced by the construct Capsid (FIG. 5B). Interestingly the dominant epitope which is induced by the construct CHIKV-E1 carries the 226A-V mutation which suggests that the construct can also effectively induce immune response against the newly emerged mutant virus. This finding may suggest that the immune response may be capable of driving the evolution of the virus through at cell selection process.

Discussion

Evaluation of the immune response induced in the C57BL/6 mice showed that the constructs were highly immunogenic and elicited T-cell immune response in the terms of an IFN-γ response and proliferation. ELISpot data from the present study suggests the magnitude of IFN-γ response was broad based in terms of the number of spots obtained. Although the envelope protein and the capsid in other related alpha viruses are known to be immunogenic, there is little knowledge about the immunogenicity of Chikungunya envelope and Capsid proteins. Elicitation of IFN-γ production from splenocytes by matrix peptide pools from different regions of the envelope E1 and Capsid identified the T cell dominant epitopes HSMTNAVTI (SEQ ID NO:18) and ACLVGDKVM (SEQ ID NO:20) in E1 and Capsid proteins respectively. Total IgG levels in vaccinated mice were found to be increased compared to that of unvaccinated controls suggesting the induction of strong humoral immune response. Subsequent studies further analyzing the type of antibody responses induced, in addition to the ability of these vaccines to drive protection against a wide range of Chikungunya virus challenges, is currently in progress.

This study suggests that these constructs could be studied further as vaccine candidates. Nonetheless, as this study is limited to the demonstration of efficient expression as well as immunogenicity after intramuscular injection of vaccine constructs followed by electroporation in mice, an elaborate evaluation of its immunogenicity in more models including the nonhuman primate model is important. The synthetic cassette constructs described appear to be a convenient tool to investigate the immunobiology of Chikungunya virus further.

Example 2

An assay was designed to measure neutralizing antibody titers which provides a feasible rapid diagnosis of clinical human CHIKV infection and for application in preclinical serosurveillance of susceptible vertebrate hosts.

CHIKV was identified by RT-PCR. RNA was extracted from the patient sera using QIAamp Viral RNA mini kit. A one-step RT-PCR test was carried out using Quiagen One step RT PCR kit. The amplification product was 305 bp within the gene that codes for the viral envelope protein E2. When cells are observed, the CHIKV causes foamy Cytopathic effect (CPE) in which rounding of cells are seen after 24-48 hours post infection (pi).

The microneutralization assay is designed as follows. The neutralization test is based on the antigen and antibody reaction. The presence of the homologous antibody towards CHIKV virus in patient serum inhibiting known viral titer is observed. Sera is diluted serially (typically for example 1:10 to 1:640) and incubated with CHIKV of a known titer under conditions and an amount of time sufficient from antibody in the sera to inhibit the virus. After incubation, the mixture is added to permissive cells under conditions that will result in viral infection of the cells if virus has not been neutralized by antibodies in the sera. The highest dilution of serum which inhibits the viral propagation is noted as antibody titer. CPE (Cytopathic effect) may be used as a measure of viral propagation in cells.

Figure 7:
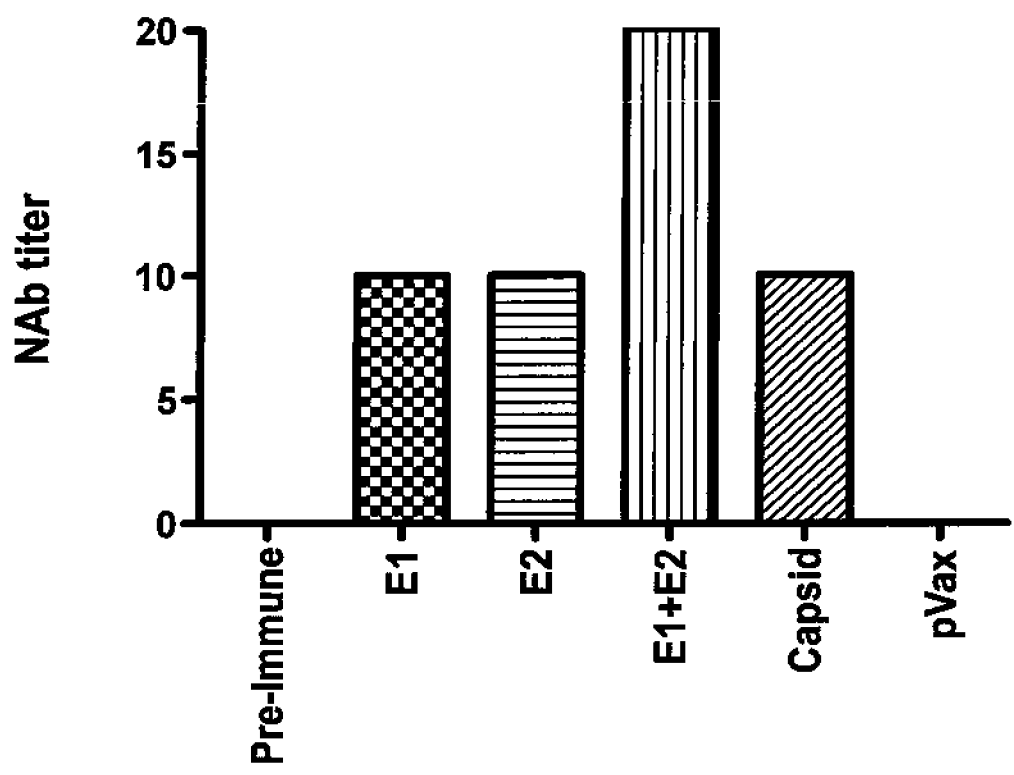
FIG. 7 is a graph showing the neutralizing antibody titers of patients and healthy individual (Naive) sera to Chikungunya virus measured using the assay described in Example 2.

The CHIKV Neutralization test was performed using patient samples. FIG. 7 is a graph showing the neutralizing antibody titers of pre-immunized and DNA immunized mice sera. Mice were immunized with constructs encoding E1, E2, Capsid, E1+E2, or the vector pVax). Sera were diluted serially (1:10 to 1:640) and incubated with CHIKV (100TC$_{ID}$50) for 90 minutes at 37° C. After incubation, the mixture was added to Vero cells (15,000 cells/well) in a 96 well flat bottom plate and incubated for 5 days at 37° C. in a 5% $CO_2$ atmosphere. The highest titer at which no CPE (Cytopathic effect) seen was recorded as Neutralizing Antibody Titer.

REFERENCES

The following references are incorporated herein by reference.

1. Strauss, J. H. and Strauss, E. G. (1994). The Alphaviruses: gene expression, replication, and evolution, Microbial. Rev. 58, 491-562.

2. Robinson, M. C. (1955). An epidemic of virus disease in Southern Province, Tanganyika Territory, in 1952-53.1. Clinical features. Trans R Soc Trap Med Hyg 49, 28-32.

3. Powers, A. M. and Logue, C. H. (2007). Changing patterns of chikungunya virus: re-emergence of a zoonotic arbovirus. Journal of General Virology vol. 88, part 9, pp. 2363-2377.

4. Porterfield, J. H. (1980). Antigenic characteristics and classification of the Togaviridae. In: Schlesinger R, editor. The Togaviruses. New York: Academic Press. 13-46.

5. Weaver, S. C. and Barrett D. T. (2004). Transmission cycles, host range, evolution and emergence of arboviral disease, Nat. Rev. Microbial. 2, pp. 789-801

6. Chevillon C, Briant L, Renaud F, Devaux C. (2008). The Chikungunya threat: an ecological and evolutionary perspective. Trends Microbial. 16 (2) 80-88.

7. Lahariya, C and Pradhan S. K. (2006). Emergence of chikungunya virus in Indian subcontinent after 32 years: a review, J. Vector Borne Dis. 43 pp. 151-160.

8. Vanlandingham D L, Hong C, Klingler K, Tsetsarkin K, McElroy K L, Powers A M, Lehane M J, Higgs S (2005). "Differential infectivities of o'nyong-nyong and chikungunya virus isolates in *Anopheles gambiae* and *Aedes aegypti* mosquitoes". Am J Trop Med Hyg 72 (5): 616-21.

9. Yergolkar, P. N. et al., (2006). Chikungunya outbreaks caused by African genotype, India, Emerg. Infect. Dis. 12; 1580-1583.

10. Warner, E., Garcia-Diaz, J., Balsamo, G., Shranatan, S., Bergmann, A., Blauwet, L., Sohail, M., Baddour, L., Reed, C. & other authors (2006). Chikungunya fever diagnosed among international travelers—United States, 2005-2006. MMWR Morb Mortal Wkly Rep 55, 1040-1042.

11. Turell, M. J., Beaman, J. R. & Tammariello, R. F. (1992). Susceptibility of selected strains of *Aedes aegypti* and *Aedes albopictus* (Diptera: Culicidae) to chikungunya virus. J Med Entomol 29, 49-53.

12. Reiter, P., Fontenille, D. & Paupy, C. (2006). *Aedes albopictus* as an epidemic vector of chikungunya virus: another emerging problem? Lancet Infect Dis 6, 463-464.

13. Johnston R E, Peters C J (1996) Alphaviruses associated primarily with fever and polyarthritis. In: Fields B N, Knipe D M, Howley P M, editors. Fields virology. Philadelphia: Lippincott-Raven Publishers. pp. 843-898.

14. Savarino A, Boelaert J R, Cassone A, Majori G, Cauda R. (2003). Effects of chloroquine on viral infections: an old drug against today's diseases? Lancet Infect Dis. 3(11):722-7.

15. Tsetsarkin K A, Vanlandingham D L, McGee C E, Higgs S. (2007). A Single Mutation in Chikungunya Virus Affects Vector Specificity and Epidemic Potential. PLoS Pathog. 7; 3(12):e201

16. Grivard P, Le Roux K, Laurent P, Fianu A, Perrau J, Gigan J, Hoarau G, Grondin N, Staikowsky F, Favier F, Michault A. (2007). Molecular and serological diagnosis of Chikungunya virus infection. Pathol Biol (Paris);55(10):490-4.

17. Vazeille-Falcoz M, Mousson L, Rodhain F, Chungue E, Fulloux A B (1999). Variation in oral susceptibility to dengue type 2 virus of populations of *Aedes .aegypti* from the islands of Tahiti and Moorea, French Polynesia. Am J Trop Med Hyg 60: 292-299.

18. Marie Vazeille et al., (2007). Two Chikungunya Isolates from the Outbreak of La Reunion (Indian Ocean) Exhibit Different Patterns of Infection in the Mosquito, *Aedes albopictus*. PLoS ONE 11: 1-9

19. Muthumani, K., A. Y. Choo, W. X. Zong, M. Madesh, D. S. Hwang, A. Premkumar, K. P. Thieu, J. Emmanuel, S. Kumar, C. B. Thompson, and D. B. Weiner. 2006. The HIV-1 Vpr and glucocorticoid receptor complex is a gain-of-function interaction that prevents the nuclear localization of PARP-1. Nat Cell Biol. 8:170-179.

20. Khan A S, Smith L C, Abruzzese R V, Cummings K K, Pope M A, Brown P A, Draghia-Akli R. (2003). Optimization of electroporation parameters for the intramuscular delivery of plasmids in pigs. DNA Cell Biol. 22(12):807-1

21. Lauren L A, Hirao L A, Wu L, Khan A S, Satishchandran A, Draghia-Akli R, Weiner D B. (2008) Intradermal/subcutaneous immunization by electrophoration improves plasmid vaccine delivery and potency in pigs and rhesus macaques. Vaccine 17; 26(3):440-8

22. Laddy D J, Yan J, Corbitt N, Kobasa D, Kobinger G P, Weiner D B. (2007) Immunogenicity of novel consensus-based DNA vaccines against avian influenza. Vaccine. 25(16):2984-9.

23. Boyer J D, Robinson T M, Kutzler M A, Vansant G, Hokey D A, Kumar S, Parkinson R, Wu L, Sidhu M K, Pavlakis G N, Felber B K, Brown C, Silvera P, Lewis M G, Monforte J, Waldmann T A, Eldridge J, Weiner D B. (2007). Protection against simian/human immunodeficiency virus (SHIV) 89.6P in macaques after coimmunization with SHIV antigen and IL-15 plasmid. Proc Natl Acad. Sci., USA. 20:104(47):18648-53

24. Feng G H, Liu N, Zhou Y, Zhai Y Z, Li X M, Dou X G (2007). Immunologic analysis induced by DNA vaccine encoding E protein of Beijing-1 strain derived from Japanese encephalitis virus. Intervirology. 50(2):93-8.

---

The invention claimed is:

1. The DNA plasmid comprising a nucleic acid sequence selected from the group consisting of:
- a nucleic acid sequence that encodes a consensus CHIKV Env including CHIKV E1 consensus protein or an immunogenic consensus fragment of CHIKV E1 consensus protein having at least 395 amino acids of CHIKV E1 consensus protein, CHIKV E2 consensus protein or an immunogenic consensus fragment of CHIKV E2 consensus protein having at least 380 amino acids of CHIKV E2 consensus protein, and CHIKV E3 consensus protein, wherein the nucleic acid-sequence that encodes CHIKV Env consensus protein comprises a nucleic acid sequence that encodes SEQ ID NO: 14 or SEQ ID NO:16;
- a nucleic acid sequence that encodes a consensus CHIKV E1 protein, wherein the nucleic acid-sequence that encodes CHIKV E1 consensus protein comprises SEQ ID NO: 1 or SEQ ID NO:4;
- a nucleic acid sequence that encodes an immunogenic consensus fragment of consensus CHIKV E1 protein having at least 395 amino acids of CHIKV E1 consensus protein, wherein the nucleic acid-sequence that encodes CHIKV E1 consensus protein comprises SEQ ID NO: 1 or SEQ ID NO:4;
- a nucleic acid sequence that encodes a consensus CHIKV E2 protein, wherein the nucleic acid-sequence that encodes CHIKV E2 consensus protein comprises SEQ ID NO:2 or SEQ ID NO:5;
- a nucleic acid sequence that encodes an immunogenic consensus fragment of consensus CHIKV E2 protein having at least 380 amino acids of CHIKV E2 consensus protein, wherein the nucleic acid-sequence that encodes CHIKV E2 consensus protein comprises SEQ ID NO:2 or SEQ ID NO:5;
- a nucleic acid sequence that encodes a consensus CHIKV capsid protein, wherein the nucleic acid-sequence that encodes CHIKV capsid consensus protein comprises SEQ ID NO :3 or SEQ ID NO:6;
- a nucleic acid sequence that encodes an immunogenic consensus fragment of consensus CHIKV capsid protein having at least 225 amino acids of CHIKV capsid consensus protein, wherein the nucleic acid-sequence that encodes CHIKV capsid consensus protein comprises SEQ ID NO:3 or SEQ ID NO:6;
- and homologues thereof having sequence homology of 95% or more.

2. A composition comprising a DNA plasmid of claim 1.

3. A composition comprising: two or more DNA plasmids of claim 1, wherein said composition comprises two or more different DNA plasmids.

4. The composition of claim 2 wherein the DNA plasmid comprises a nucleic acid sequence that encodes CHIKV E1 consensus protein; wherein the nucleic acid-sequence that encodes CHIKV E1 consensus protein comprises SEQ ID NO:1 or SEQ ID NO:4.

5. The composition claim 2 wherein the DNA plasmid comprises a nucleic acid sequence that encodes CHIKV E2 consensus protein, wherein the nucleic acid-sequence that encodes CHIKV E2 consensus protein comprises SEQ ID NO:2 or SEQ ID NO:5.

6. The composition claim 2 wherein the DNA plasmid comprises a nucleic acid sequence that encodes CHIKV capsid consensus protein, wherein the nucleic acid-sequence that encodes CHIKV capsid consensus protein comprises SEQ ID NO:3 or SEQ ID NO:6.

7. The DNA plasmid of claim 1 comprising a nucleic acid sequence that encodes a consensus CHIKV Env protein; wherein the nucleic acid-sequence that encodes CHIKV E1 consensus protein comprises SEQ ID NO:13 or SEQ ID NO:15.

8. The composition of claim 2 wherein the DNA plasmid comprises a nucleic acid sequence that encodes an IgE leader sequence, wherein said nucleic acid sequence that encodes said leader sequence is operatively linked to said CHIKV nucleic acid sequence.

9. An injectable pharmaceutical composition comprising the composition of claim 2.

10. A method of inducing an immune response in an individual against CHIKV comprising administering to said individual a composition of claim 2.

11. The method of claim 10 wherein said composition is administering using electroporation.

12. The DNA plasmid of claim 1 wherein said homologues thereof have sequence homology of 98% or more.

13. The DNA plasmid of claim 1 wherein said homologues thereof have sequence homology of 99% or more.

14. The composition of claim 2 wherein said homologues thereof have sequence homology of 98% or more.

15. The composition of claim 2 wherein said homologues thereof have sequence homology of 99% or more.

16. The DNA plasmid of claim 1 comprising a nucleic acid sequence selected from the group consisting of:
   a nucleic acid sequence that encodes a consensus CHIKV Env including CHIKV E1 consensus protein or an immunogenic consensus fragment of CHIKV E1 consensus protein having at least 395 amino acids of CHIKV E1 consensus protein, CHIKV E2 consensus protein or an immunogenic consensus fragment of CHIKV E2 consensus protein having at least 380 amino acids of CHIKV E2 consensus protein, and CHIKV E3 consensus protein, wherein the nucleic acid-sequence that encodes CHIKV Env consensus protein comprises a nucleic acid sequence that encodes SEQ ID NO: 14 or SEQ ID NO:16;
   a nucleic acid sequence that encodes a consensus CHIKV E 1 protein, wherein the nucleic acid-sequence that encodes CHIKV E1 consensus protein comprises SEQ ID NO: 1 or SEQ ID NO:4;
   a nucleic acid sequence that encodes an immunogenic consensus fragment of consensus CHIKV E1 protein having at least 395 amino acids of CHIKV E1 consensus protein, wherein the nucleic acid-sequence that encodes CHIKV E1 consensus protein comprises SEQ ID NO: 1 or SEQ ID NO:4;
   a nucleic acid sequence that encodes a consensus CHIKV E2 protein, wherein the nucleic acid-sequence that encodes CHIKV E2 consensus protein comprises SEQ ID NO:2 or SEQ ID NO:5;
   a nucleic acid sequence that encodes an immunogenic consensus fragment of consensus CHIKV E2 protein having at least 380 amino acids of CHIKV E2 consensus protein, wherein the nucleic acid-sequence that encodes CHIKV E2 consensus protein comprises SEQ ID NO:2 or SEQ ID NO:5;
   a nucleic acid sequence that encodes a consensus CHIKV capsid protein, wherein the nucleic acid-sequence that encodes CHIKV capsid consensus protein comprises SEQ ID NO :3 or SEQ ID NO:6; and a nucleic acid sequence that encodes an immunogenic consensus fragment of consensus CHIKV capsid protein having at least 225 amino acids of CHIKV capsid consensus protein, wherein the nucleic acid-sequence that encodes CHIKV capsid consensus protein comprises SEQ ID NO:3 or SEQ ID NO:6.

17. The DNA plasmid of claim 16 comprising a nucleic acid sequence selected from the group consisting of:
   a nucleic acid sequence that encodes a consensus CHIKV Env including CHIKV E1 consensus protein, CHIKV E2 consensus protein, and CHIKV E3 consensus protein, wherein the nucleic acid-sequence that encodes CHIKV Env consensus protein comprises a nucleic acid sequence that encodes SEQ ID NO:14 or SEQ ID NO:16;
   a nucleic acid sequence that encodes a consensus CHIKV E1 protein, wherein the nucleic acid-sequence that encodes CHIKV E1 consensus protein comprises SEQ ID NO:1 or SEQ ID NO:4;
   a nucleic acid sequence that encodes a consensus CHIKV E2 protein, wherein the nucleic acid-sequence that encodes CHIKV E2 consensus protein comprises SEQ ID NO:2 or SEQ ID NO:5; and
   a nucleic acid sequence that encodes a consensus CHIKV capsid protein, wherein the nucleic acid-sequence that encodes CHIKV capsid consensus protein comprises SEQ ID NO:3 or SEQ ID NO:6.

18. The DNA plasmid of claim 17 comprising a nucleic acid sequence that encodes a consensus CHIKV E1 protein, wherein the nucleic acid-sequence that encodes CHIKV E1 consensus protein comprises SEQ ID NO:1 or SEQ ID NO:4.

19. The DNA plasmid of claim 17 comprising a nucleic acid sequence that encodes a consensus CHIKV E2 protein, wherein the nucleic acid-sequence that encodes CHIKV E2 consensus protein comprises SEQ ID NO:2 or SEQ ID NO:5.

20. The DNA plasmid of claim 17 comprising a nucleic acid sequence that encodes a consensus CHIKV capsid protein, wherein the nucleic acid-sequence that encodes CHIKV capsid consensus protein comprises SEQ ID NO:3 or SEQ ID NO:6.

\* \* \* \* \*

SEQUENCE LISTING

<160> NUMBER OF SEQ ID NOS: 20

<210> SEQ ID NO 1
<211> LENGTH: 1374
<212> TYPE: DNA
<213> ORGANISM: Artificial Sequence
<220> FEATURE:
<223> OTHER INFORMATION: CHIKV E1 consensus

<400> SEQUENCE: 1

```
atggactgga cctggatcct gtttctggtc gctgctgcca cccgggtgca cagctacgag      60
cacgtgaccg tgatccccaa caccgtgggc gtgccctaca agaccctggt gaacaggccc     120
ggctacagcc ccatggtgct ggaaatggaa ctgctgtccg tgaccctgga acccaccctg     180
agcctggact acatcacctg cgagtacaag acagtgatcc ccagcccta cgtgaagtgc     240 tgcggcaccg ccgagtgcaa ggacaagaac ctgcccgact acagctgcaa ggtgttcacc      300
```

-continued

```
ggcgtgtacc ccttcatgtg gggcggagcc tactgcttct gcgacgccga gaacacccag    360
ctgtccgagg cccacgtgga gaagagcgag agctgcaaga ccgagttcgc cagcgcctac    420
cgggcccaca cagccagcgc cagcgccaag ctgcgggtgc tgtaccaggg caacaacatc    480
accgtgaccg cctacgccaa cggcgaccac gccgtgacag tgaaggacgc caagttcatc    540
gtgggcccca tgagcagcgc ctggaccccc ttcgacaaca agatcgtggt gtacaagggc    600
gacgtgtaca acatggacta cccccccttc ggagccggca gacccggcca gttcggcgac    660
atccagagcc ggacccccga gagcaaggac gtgtacgcca atacccagct ggtgctgcag    720
agacccgccg tgggcaccgt gcacgtgcct tacagccagg cccccagcgg cttcaagtac    780
tggctgaaag agaggggcgc cagcctgcag cacaccgccc ccttcggctg ccagatcgcc    840
accaaccccg tgcgggccgt gaattgtgcc gtgggcaaca tgcccatcag catcgacatc    900
cccgaggccg ccttcaccag ggtggtggac gcccccagcc tgaccgacat gagctgcgag    960
gtgcccgcct gcacccacag cagcgacttc ggcggcgtgg ccatcatcaa gtacgccgcc   1020
agcaagaaag gcaagtgcgc cgtgcacagc atgaccaatg ccgtgaccat ccgggaggcc   1080
gagatcgagg tggagggcaa cagccagctg cagatcagct tcagcaccgc cctggccagc   1140
gccgagttcc gggtgcaggt ctgcagcacc caggtgcact gtgccgccga gtgtcacccc   1200
cccaaggacc acatcgtgaa ctaccccgcc agccacacca ccctgggcgt gcaggacatc   1260
agcgccaccg ccatgagctg ggtgcagaag atcacaggcg gcgtcggcct ggtggtggcc   1320
gtggccgccc tgatcctgat cgtggtgctg tgcgtgagct tcagccggca ctga         1374
```

<210> SEQ ID NO 2
<211> LENGTH: 1326
<212> TYPE: DNA
<213> ORGANISM: Artificial Sequence
<220> FEATURE:
<223> OTHER INFORMATION: CHIKV E2 consensus

<400> SEQUENCE: 2

```
atggactgga cctggatcct gttcctggtc gctgctgcca caagagtgca cagcagcacc     60
aaggacaact tcaacgtgta caaggccacc cggccctacc tggcccactg ccccgattgc    120
ggcgagggcc acagctgcca cagccccgtg gccctggaac ggatccggaa cgaggccacc    180
gacggcaccc tgaagatcca ggtgtccctg cagatcggca tcaagaccga cgacagccac    240
gactggacca agctgcggta catggacaac cacatgcccg ccgacgccga gagagccggc    300
ctgttcgtcc ggaccagcgc cccctgcacc atcaccggca ccatgggcca cttcatcctg    360
gcccggtgcc ccaagggcga gacactgacc gtgggcttca ccgacagccg gaagatcagc    420
cactcctgca cccacccctt ccaccacgac ccccccgtga tcggccggga gaagttccac    480
agcaggcccc agcacggcaa agagctgccc tgcagcacct acgtgcagag caccgccgcc    540
acaaccgagg aaatcgaggt gcacatgccc cccgataccc ccgaccggac cctgatgagc    600
cagcagagcg gcaacgtgaa gatcaccgtg aacggccaga ccgtgcggta caagtgcaac    660
tgcggcggca gcaacgaggg cctgaccacc accgacaagg tgatcaacaa ctgcaaggtg    720
gaccagtgcc acgccgccgt gaccaaccac aagaagtggc agtacaacag ccccctggtg    780
ccccggaatg ccgagctggg cgaccggaag ggcaagatcc acatcccctt cccccctggcc   840
aacgtgacct gccgggtgcc caaggcccgg aaccccaccg tgacctacgg caagaaccag    900
gtgatcatgc tgctgtaccc cgaccacccc accctgctgt cctaccggaa catgggcgag    960
gaacccaact accaagagga gtgggtcatg cacaagaaag aagtggtgct gaccgtcccc   1020
```

```
accgagggcc tggaagtgac ctggggcaac aacgagccct acaagtactg gccccagctg     1080
tccaccaacg gcaccgccca cggccacccc cacgagatca tcctgtacta ctacgagctg     1140
taccctacca tgaccgtggt ggtggtgtcc gtggccacct ttatcctgct gtccatggtc     1200
ggcatggccc tggcatgtgt catgtgcgcc aggaggcgct gtatcacccc ctacgagctg     1260
acacctggcg ccaccgtgcc ctttctgctg tccctgatct gctgcatccg gaccgccaag     1320
gcctga                                                                1326

<210> SEQ ID NO 3
<211> LENGTH: 840
<212> TYPE: DNA
<213> ORGANISM: Artificial Sequence
<220> FEATURE:
<223> OTHER INFORMATION: CHIKV capsid consensus

<400> SEQUENCE: 3
atggactgga cctggatcct gttcctggtg gccgctgcca cccgggtgca cagcatggaa       60
ttcatcccca cccagacctt ctacaaccgg cgctaccagc ccagaccctg gacccccagg      120
cccaccatcc aggtgatccg gcccaggccc agacccagag gcaggccggg cagctggca      180 cagctgatca gcgccgtgaa caagctgacc atgagagccg tgccccagca aagcccagg      240 cggaaccgga gaacaagaa gcagaagcag aaacagcagg ccccccagaa caacaccaac       300
cagaagaagc agcccccaa gaagaagcct gcccagaaga gaagaaaccc ggcaggcgg       360 gagcggatgt gcatgaagat cgagaacgac tgcatcttcg aggtgaagca cgagggcaag      420
gtgaccggct acgcctgcct ggtcggcgac aaagtgatga gcccgccca cgtgaaggc      480 accatcgaca cgccgacct ggccaagctg gccttcaagc ggagcagcaa gtacgacctg       540
gaatgcgccc agatccccgt gcacatgaag agcgacgcca gcaagttcac ccacgagaag      600
cccgagggct actacaactg caccacggga ccgtgcagt acagcggcgg caggttcacc      660
atccccacag gcgccggaaa gcccggcgac agcggcaggc ccatcttcga caacaagggc       720
cgggtggtgg ccatcgtgct gggcggagcc aacgagggcg ccaggaccgc cctgagcgtg      780
gtgacctgga acaaggacat cgtgaccaag atcacccccg agggcgccga agagtggtga      840

<210> SEQ ID NO 4
<211> LENGTH: 1320
<212> TYPE: DNA
<213> ORGANISM: Artificial Sequence
<220> FEATURE:
<223> OTHER INFORMATION: CHIKV E1 consensus

<400> SEQUENCE: 4
tacgagcacg tgaccgtgat ccccaacacc gtgggcgtgc cctacaagac cctggtgaac       60
aggcccggct acagccccat ggtgctggaa atggaactgc tgtccgtgac cctggaaccc      120
accctgagcc tggactacat cacctgcgag tacaagacag tgatccccag ccctacgtg      180 aagtgctgcg gcaccgccga gtgcaaggac aagaacctgc ccgactacag ctgcaaggtg      240
ttcaccggcg tgtacccctt catgtggggc ggagcctact gcttctgcga cgccgagaac      300
acccagctgt ccgaggccca cgtggagaag agcgagagct gcaagaccga gttcgccagc      360
gcctaccggg cccacacagc cagcgccagc gccaagctgc gggtgctgta ccagggcaac       420
aacatcaccg tgaccgccta cgccaacggc gaccacgccg tgacagtgaa ggacgccaag      480
ttcatcgtgg gccccatgag cagcgcctgg acccccttcg acaacaagat cgtggtgtac      540
```

```
aagggcgacg tgtacaacat ggactacccc cccttcggag ccggcagacc cggccagttc      600
ggcgacatcc agagccggac ccccgagagc aaggacgtgt acgccaatac ccagctggtg      660
ctgcagagac ccgccgtggg caccgtgcac gtgccttaca gccaggcccc cagcggcttc      720
aagtactggc tgaaagagag gggcgccagc ctgcagcaca ccgccccctt cggctgccag      780
atcgccacca ccccgtgcg ggccgtgaat tgtgccgtgg gcaacatgcc catcagcatc       840 gacatcccg aggccgcctt caccagggtg gtggacgccc ccagcctgac cgacatgagc        900
tgcgaggtgc ccgcctgcac ccacagcagc gacttcggcg gcgtggccat catcaagtac      960
gccgccagca agaaaggcaa gtgcgccgtg cacagcatga ccaatgccgt gaccatccgg      1020
gaggccgaga tcgaggtgga gggcaacagc cagctgcaga tcagcttcag caccgccctg      1080
gccagcgccg agttccgggt gcaggtctgc agcacccagg tgcactgtgc cgccgagtgt     1140 cacccccca aggaccacat cgtgaactac cccgccagcc acaccaccct gggcgtgcag       1200
gacatcagcg ccaccgccat gagctgggtg cagaagatca caggcggcgt cggcctggtg     1260
gtggccgtgg ccgccctgat cctgatcgtg gtgctgtgcg tgagcttcag ccggcactga     1320
```

<210> SEQ ID NO 5
<211> LENGTH: 1273
<212> TYPE: DNA
<213> ORGANISM: Artificial Sequence
<220> FEATURE:
<223> OTHER INFORMATION: CHIKV E2 consensus

<400> SEQUENCE: 5

```
cagcaccaag acaacttca acgtgtacaa ggccacccgg ccctacctgg cccactgccc       60
cgattgcggc gagggccaca gctgccacag ccccgtggcc ctggaacgga tccggaacga     120
ggccaccgac ggcacccctga agatccaggt gtccctgcag atcggcatca agaccgacga    180
cagccacgac tggaccaagc tgcggtacat ggacaaccac atgcccgccg acgccgagag    240
agccggcctg ttcgtccgga ccagcgcccc ctgcaccatc accggcacca tgggccactt    300
catcctggcc cggtgcccca agggcgagac actgaccgtg ggcttcaccg acagccggaa    360
gatcagccac tcctgcaccc accccttcca ccacgacccc cccgtgatcg ccgggagaa     420 gttccacagc aggccccagc acggcaaaga gctgccctgc agcacctacg tgcagagcac    480
cgccgccaca accgaggaaa tcgaggtgca catgcccccc gataccccg accggaccct     540 gatgagccag cagagcggca acgtgaagat caccgtgaac ggccagaccg tgcggtacaa    600
gtgcaactgc ggcggcagca acgagggcct gaccaccacc gacaaggtga tcaacaactg    660
caaggtggac cagtgccacg ccgccgtgac caaccacaag aagtggcagt acaacagccc    720
cctggtgccc cggaatgccg agctgggcga ccggaagggc aagatccaca tcccttccc    780 cctggccaac gtgaccctgcc gggtgcccaa ggcccggaac ccaccgtga cctacggcaa    840 gaaccaggtg atcatgctgc tgtaccccga ccaccccacc ctgctgtcct accggaacat    900
gggcgaggaa cccaactacc aagaggagtg ggtcatgcac aagaaagaag tggtgctgac    960
cgtccccacc gagggcctgg aagtgacctg gggcaacaac gagccctaca gtactggcc    1020 ccagctgtcc accaacggca ccgccccacg ccacccccac gagatcatcc tgtactacta    1080
cgagctgtac cctaccatga ccgtggtggt ggtgtccgtg gccaccttta tcctgctgtc    1140
catggtcggc atggccgctg gcatgtgcat gtgcgccagg aggcgctgta tcaccccta     1200 cgagctgaca cctggcgcca ccgtgccctt tctgctgtcc ctgatctgct gcatccggac    1260
cgccaaggcc tga                                                        1273
```

<210> SEQ ID NO 6
<211> LENGTH: 786
<212> TYPE: DNA
<213> ORGANISM: Artificial Sequence
<220> FEATURE:
<223> OTHER INFORMATION: CHIKV capsid consensus

<400> SEQUENCE: 6

```
atggaattca tccccaccca gaccttctac aaccggcgct accagcccag accctggacc      60
cccaggccca ccatccaggt gatccggccc aggcccagac cccagaggca ggccgggcag     120
ctggcacagc tgatcagcgc cgtgaacaag ctgaccatga gaccgtgcc ccagcagaag      180
cccaggcgga accggaagaa caagaagcag aagcagaaac agcaggcccc ccagaacaac     240
accaaccaga agaagcagcc ccccaagaag aagcctgccc agaagaagaa gaaacccggc     300
aggcgggagc ggatgtgcat gaagatcgag aacgactgca tcttcgaggt gaagcacgag     360
ggcaaggtga ccggctacgc ctgcctggtc ggcgacaaag tgatgaagcc cgcccacgtg     420
aagggcacca tcgacaacgc cgacctggcc aagctggcct tcaagcggag cagcaagtac     480
gacctggaat cgcccagat ccccgtgcac atgaagagcg acgccagcaa gttcacccac      540
gagaagcccg agggctacta caactggcac cacggagccg tgcagtacag cggcggcagg     600
ttcaccatcc ccacaggcgc cggaaagccc ggcgacagcg caggcccat cttcgacaac      660
aagggccggg tggtggccat cgtgctgggc ggagccaacg agggcgccag gaccgccctg     720
agcgtggtga cctggaacaa ggacatcgtg accaagatca cccccgaggg cgccgaagag     780
tggtga                                                                786
```

<210> SEQ ID NO 7
<211> LENGTH: 457
<212> TYPE: PRT
<213> ORGANISM: Artificial Sequence
<220> FEATURE:
<223> OTHER INFORMATION: CHIKV E1 consensus

<400> SEQUENCE: 7

```
Met Asp Trp Thr Trp Ile Leu Phe Leu Val Ala Ala Thr Arg Val
1               5                   10                  15

His Ser Tyr Glu His Val Thr Val Ile Pro Asn Thr Val Gly Val Pro
            20                  25                  30

Tyr Lys Thr Leu Val Asn Arg Pro Gly Tyr Ser Pro Met Val Leu Glu
        35                  40                  45

Met Glu Leu Leu Ser Val Thr Leu Glu Pro Thr Leu Ser Leu Asp Tyr
    50                  55                  60

Ile Thr Cys Glu Tyr Lys Thr Val Ile Pro Ser Pro Tyr Val Lys Cys
65                  70                  75                  80

Cys Gly Thr Ala Glu Cys Lys Asp Lys Asn Leu Pro Asp Tyr Ser Cys
                85                  90                  95

Lys Val Phe Thr Gly Val Tyr Pro Phe Met Trp Gly Gly Ala Tyr Cys
            100                 105                 110

Phe Cys Asp Ala Glu Asn Thr Gln Leu Ser Glu Ala His Val Glu Lys
        115                 120                 125

Ser Glu Ser Cys Lys Thr Glu Phe Ala Ser Ala Tyr Arg Ala His Thr
    130                 135                 140

Ala Ser Ala Ser Ala Lys Leu Arg Val Leu Tyr Gln Gly Asn Asn Ile
145                 150                 155                 160
```

-continued

```
Thr Val Thr Ala Tyr Ala Asn Gly Asp His Ala Val Thr Val Lys Asp
                165                 170                 175
Ala Lys Phe Ile Val Gly Pro Met Ser Ser Ala Trp Thr Pro Phe Asp
            180                 185                 190
Asn Lys Ile Val Val Tyr Lys Gly Asp Val Tyr Asn Met Asp Tyr Pro
        195                 200                 205
Pro Phe Gly Ala Gly Arg Pro Gly Gln Phe Gly Asp Ile Gln Ser Arg
    210                 215                 220
Thr Pro Glu Ser Lys Asp Val Tyr Ala Asn Thr Gln Leu Val Leu Gln
225                 230                 235                 240
Arg Pro Ala Val Gly Thr Val His Val Pro Tyr Ser Gln Ala Pro Ser
                245                 250                 255
Gly Phe Lys Tyr Trp Leu Lys Glu Arg Gly Ala Ser Leu Gln His Thr
            260                 265                 270
Ala Pro Phe Gly Cys Gln Ile Ala Thr Asn Pro Val Arg Ala Val Asn
        275                 280                 285
Cys Ala Val Gly Asn Met Pro Ile Ser Ile Asp Ile Pro Glu Ala Ala
    290                 295                 300
Phe Thr Arg Val Val Asp Ala Pro Ser Leu Thr Asp Met Ser Cys Glu
305                 310                 315                 320
Val Pro Ala Cys Thr His Ser Ser Asp Phe Gly Gly Val Ala Ile Ile
                325                 330                 335
Lys Tyr Ala Ala Ser Lys Lys Gly Lys Cys Ala Val His Ser Met Thr
            340                 345                 350
Asn Ala Val Thr Ile Arg Glu Ala Glu Ile Glu Val Glu Gly Asn Ser
        355                 360                 365
Gln Leu Gln Ile Ser Phe Ser Thr Ala Leu Ala Ser Ala Glu Phe Arg
    370                 375                 380
Val Gln Val Cys Ser Thr Gln Val His Cys Ala Ala Glu Cys His Pro
385                 390                 395                 400
Pro Lys Asp His Ile Val Asn Tyr Pro Ala Ser His Thr Thr Leu Gly
                405                 410                 415
Val Gln Asp Ile Ser Ala Thr Ala Met Ser Trp Val Gln Lys Ile Thr
            420                 425                 430
Gly Gly Val Gly Leu Val Val Ala Val Ala Ala Leu Ile Leu Ile Val
        435                 440                 445
Val Leu Cys Val Ser Phe Ser Arg His
    450                 455

<210> SEQ ID NO 8
<211> LENGTH: 441
<212> TYPE: PRT
<213> ORGANISM: Artificial Sequence
<220> FEATURE:
<223> OTHER INFORMATION: CHIKV E2 consensus

<400> SEQUENCE: 8

Met Asp Trp Thr Trp Ile Leu Phe Leu Val Ala Ala Ala Thr Arg Val
1               5                   10                  15
His Ser Ser Thr Lys Asp Asn Phe Asn Val Tyr Lys Ala Thr Arg Pro
                20                  25                  30
Tyr Leu Ala His Cys Pro Asp Cys Gly Glu Gly His Ser Cys His Ser
            35                  40                  45
Pro Val Ala Leu Glu Arg Ile Arg Asn Glu Ala Thr Asp Gly Thr Leu
        50                  55                  60
```

```
Lys Ile Gln Val Ser Leu Gln Ile Gly Ile Lys Thr Asp Asp Ser His
 65                  70                  75                  80

Asp Trp Thr Lys Leu Arg Tyr Met Asp Asn His Met Pro Ala Asp Ala
                 85                  90                  95

Glu Arg Ala Gly Leu Phe Val Arg Thr Ser Ala Pro Cys Thr Ile Thr
            100                 105                 110

Gly Thr Met Gly His Phe Ile Leu Ala Arg Cys Pro Lys Gly Glu Thr
            115                 120                 125

Leu Thr Val Gly Phe Thr Asp Ser Arg Lys Ile Ser His Ser Cys Thr
        130                 135                 140

His Pro Phe His His Asp Pro Pro Val Ile Gly Arg Glu Lys Phe His
145                 150                 155                 160

Ser Arg Pro Gln His Gly Lys Glu Leu Pro Cys Ser Thr Tyr Val Gln
                165                 170                 175

Ser Thr Ala Ala Thr Thr Glu Glu Ile Glu Val His Met Pro Pro Asp
            180                 185                 190

Thr Pro Asp Arg Thr Leu Met Ser Gln Gln Ser Gly Asn Val Lys Ile
        195                 200                 205

Thr Val Asn Gly Gln Thr Val Arg Tyr Lys Cys Asn Cys Gly Gly Ser
210                 215                 220

Asn Glu Gly Leu Thr Thr Thr Asp Lys Val Ile Asn Asn Cys Lys Val
225                 230                 235                 240

Asp Gln Cys His Ala Ala Val Thr Asn His Lys Lys Trp Gln Tyr Asn
                245                 250                 255

Ser Pro Leu Val Pro Arg Asn Ala Glu Leu Gly Asp Arg Lys Gly Lys
            260                 265                 270

Ile His Ile Pro Phe Pro Leu Ala Asn Val Thr Cys Arg Val Pro Lys
        275                 280                 285

Ala Arg Asn Pro Thr Val Thr Tyr Gly Lys Asn Gln Val Ile Met Leu
290                 295                 300

Leu Tyr Pro Asp His Pro Thr Leu Leu Ser Tyr Arg Asn Met Gly Glu
305                 310                 315                 320

Glu Pro Asn Tyr Gln Glu Glu Trp Val Met His Lys Lys Glu Val Val
                325                 330                 335

Leu Thr Val Pro Thr Glu Gly Leu Glu Val Thr Trp Gly Asn Asn Glu
            340                 345                 350

Pro Tyr Lys Tyr Trp Pro Gln Leu Ser Thr Asn Gly Thr Ala His Gly
        355                 360                 365

His Pro His Glu Ile Ile Leu Tyr Tyr Tyr Glu Leu Tyr Pro Thr Met
370                 375                 380

Thr Val Val Val Ser Val Ala Thr Phe Ile Leu Leu Ser Met Val
385                 390                 395                 400

Gly Met Ala Ala Gly Met Cys Met Cys Ala Arg Arg Arg Cys Ile Thr
                405                 410                 415

Pro Tyr Glu Leu Thr Pro Gly Ala Thr Val Pro Phe Leu Leu Ser Leu
            420                 425                 430

Ile Cys Cys Ile Arg Thr Ala Lys Ala
        435                 440

<210> SEQ ID NO 9
<211> LENGTH: 279
<212> TYPE: PRT
<213> ORGANISM: Artificial Sequence
<220> FEATURE:
<223> OTHER INFORMATION: CHIKV capsid consensus
```

<400> SEQUENCE: 9

Met Asp Trp Thr Trp Ile Leu Phe Leu Val Ala Ala Ala Thr Arg Val
1               5                   10                  15

His Ser Met Glu Phe Ile Pro Thr Gln Thr Phe Tyr Asn Arg Arg Tyr
            20                  25                  30

Gln Pro Arg Pro Trp Thr Pro Arg Pro Thr Ile Gln Val Ile Arg Pro
        35                  40                  45

Arg Pro Arg Pro Gln Arg Gln Ala Gly Gln Leu Ala Gln Leu Ile Ser
    50                  55                  60

Ala Val Asn Lys Leu Thr Met Arg Ala Val Pro Gln Gln Lys Pro Arg
65                  70                  75                  80

Arg Asn Arg Lys Asn Lys Lys Gln Lys Gln Lys Gln Gln Ala Pro Gln
                85                  90                  95

Asn Asn Thr Asn Gln Lys Lys Gln Pro Pro Lys Lys Lys Pro Ala Gln
            100                 105                 110

Lys Lys Lys Lys Pro Gly Arg Arg Glu Arg Met Cys Met Lys Ile Glu
        115                 120                 125

Asn Asp Cys Ile Phe Glu Val Lys His Glu Gly Lys Val Thr Gly Tyr
    130                 135                 140

Ala Cys Leu Val Gly Asp Lys Val Met Lys Pro Ala His Val Lys Gly
145                 150                 155                 160

Thr Ile Asp Asn Ala Asp Leu Ala Lys Leu Ala Phe Lys Arg Ser Ser
                165                 170                 175

Lys Tyr Asp Leu Glu Cys Ala Gln Ile Pro Val His Met Lys Ser Asp
            180                 185                 190

Ala Ser Lys Phe Thr His Glu Lys Pro Glu Gly Tyr Tyr Asn Trp His
        195                 200                 205

His Gly Ala Val Gln Tyr Ser Gly Gly Arg Phe Thr Ile Pro Thr Gly
    210                 215                 220

Ala Gly Lys Pro Gly Asp Ser Gly Arg Pro Ile Phe Asp Asn Lys Gly
225                 230                 235                 240

Arg Val Val Ala Ile Val Leu Gly Gly Ala Asn Glu Gly Ala Arg Thr
                245                 250                 255

Ala Leu Ser Val Val Thr Trp Asn Lys Asp Ile Val Thr Lys Ile Thr
            260                 265                 270

Pro Glu Gly Ala Glu Glu Trp
        275

<210> SEQ ID NO 10
<211> LENGTH: 439
<212> TYPE: PRT
<213> ORGANISM: Artificial Sequence
<220> FEATURE:
<223> OTHER INFORMATION: CHIKV E1 consensus

<400> SEQUENCE: 10

Tyr Glu His Val Thr Val Ile Pro Asn Thr Val Gly Val Pro Tyr Lys
1               5                   10                  15

Thr Leu Val Asn Arg Pro Gly Tyr Ser Pro Met Val Leu Glu Met Glu
            20                  25                  30

Leu Leu Ser Val Thr Leu Glu Pro Thr Leu Ser Leu Asp Tyr Ile Thr
        35                  40                  45

Cys Glu Tyr Lys Thr Val Ile Pro Ser Pro Tyr Val Lys Cys Cys Gly
    50                  55                  60

```
Thr Ala Glu Cys Lys Asp Lys Asn Leu Pro Asp Tyr Ser Cys Lys Val
 65                  70                  75                  80

Phe Thr Gly Val Tyr Pro Phe Met Trp Gly Gly Ala Tyr Cys Phe Cys
                 85                  90                  95

Asp Ala Glu Asn Thr Gln Leu Ser Glu Ala His Val Glu Lys Ser Glu
            100                 105                 110

Ser Cys Lys Thr Glu Phe Ala Ser Ala Tyr Arg Ala His Thr Ala Ser
        115                 120                 125

Ala Ser Ala Lys Leu Arg Val Leu Tyr Gln Gly Asn Asn Ile Thr Val
130                 135                 140

Thr Ala Tyr Ala Asn Gly Asp His Ala Val Thr Val Lys Asp Ala Lys
145                 150                 155                 160

Phe Ile Val Gly Pro Met Ser Ser Ala Trp Thr Pro Phe Asp Asn Lys
                165                 170                 175

Ile Val Val Tyr Lys Gly Asp Val Tyr Asn Met Asp Tyr Pro Pro Phe
                180                 185                 190

Gly Ala Gly Arg Pro Gly Gln Phe Gly Asp Ile Gln Ser Arg Thr Pro
            195                 200                 205

Glu Ser Lys Asp Val Tyr Ala Asn Thr Gln Leu Val Leu Gln Arg Pro
        210                 215                 220

Ala Val Gly Thr Val His Val Pro Tyr Ser Gln Ala Pro Ser Gly Phe
225                 230                 235                 240

Lys Tyr Trp Leu Lys Glu Arg Gly Ala Ser Leu Gln His Thr Ala Pro
                245                 250                 255

Phe Gly Cys Gln Ile Ala Thr Asn Pro Val Arg Ala Val Asn Cys Ala
                260                 265                 270

Val Gly Asn Met Pro Ile Ser Ile Asp Ile Pro Glu Ala Ala Phe Thr
            275                 280                 285

Arg Val Val Asp Ala Pro Ser Leu Thr Asp Met Ser Cys Glu Val Pro
        290                 295                 300

Ala Cys Thr His Ser Ser Asp Phe Gly Gly Val Ala Ile Ile Lys Tyr
305                 310                 315                 320

Ala Ala Ser Lys Lys Gly Lys Cys Ala Val His Ser Met Thr Asn Ala
                325                 330                 335

Val Thr Ile Arg Glu Ala Glu Ile Glu Val Glu Gly Asn Ser Gln Leu
                340                 345                 350

Gln Ile Ser Phe Ser Thr Ala Leu Ala Ser Ala Glu Phe Arg Val Gln
            355                 360                 365

Val Cys Ser Thr Gln Val His Cys Ala Ala Glu Cys His Pro Pro Lys
        370                 375                 380

Asp His Ile Val Asn Tyr Pro Ala Ser His Thr Thr Leu Gly Val Gln
385                 390                 395                 400

Asp Ile Ser Ala Thr Ala Met Ser Trp Val Gln Lys Ile Thr Gly Gly
                405                 410                 415

Val Gly Leu Val Val Ala Val Ala Ala Leu Ile Leu Ile Val Val Leu
            420                 425                 430

Cys Val Ser Phe Ser Arg His
        435

<210> SEQ ID NO 11
<211> LENGTH: 423
<212> TYPE: PRT
<213> ORGANISM: Artificial Sequence
<220> FEATURE:
<223> OTHER INFORMATION: CHIKV E2 consensus
```

<400> SEQUENCE: 11

```
Ser Thr Lys Asp Asn Phe Asn Val Tyr Lys Ala Thr Arg Pro Tyr Leu
 1               5                  10                  15

Ala His Cys Pro Asp Cys Gly Glu Gly His Ser Cys His Ser Pro Val
            20                  25                  30

Ala Leu Glu Arg Ile Arg Asn Glu Ala Thr Asp Gly Thr Leu Lys Ile
        35                  40                  45

Gln Val Ser Leu Gln Ile Gly Ile Lys Thr Asp Ser His Asp Trp
    50                  55                  60

Thr Lys Leu Arg Tyr Met Asp Asn His Met Pro Ala Asp Ala Glu Arg
65                  70                  75                  80

Ala Gly Leu Phe Val Arg Thr Ser Ala Pro Cys Thr Ile Thr Gly Thr
                85                  90                  95

Met Gly His Phe Ile Leu Ala Arg Cys Pro Lys Gly Glu Thr Leu Thr
            100                 105                 110

Val Gly Phe Thr Asp Ser Arg Lys Ile Ser His Ser Cys Thr His Pro
        115                 120                 125

Phe His His Asp Pro Pro Val Ile Gly Arg Glu Lys Phe His Ser Arg
    130                 135                 140

Pro Gln His Gly Lys Glu Leu Pro Cys Ser Thr Tyr Val Gln Ser Thr
145                 150                 155                 160

Ala Ala Thr Thr Glu Glu Ile Glu Val His Met Pro Pro Asp Thr Pro
                165                 170                 175

Asp Arg Thr Leu Met Ser Gln Gln Ser Gly Asn Val Lys Ile Thr Val
            180                 185                 190

Asn Gly Gln Thr Val Arg Tyr Lys Cys Asn Cys Gly Gly Ser Asn Glu
        195                 200                 205

Gly Leu Thr Thr Thr Asp Lys Val Ile Asn Cys Lys Val Asp Gln
    210                 215                 220

Cys His Ala Ala Val Thr Asn His Lys Lys Trp Gln Tyr Asn Ser Pro
225                 230                 235                 240

Leu Val Pro Arg Asn Ala Glu Leu Gly Asp Arg Lys Gly Lys Ile His
                245                 250                 255

Ile Pro Phe Pro Leu Ala Asn Val Thr Cys Arg Val Pro Lys Ala Arg
            260                 265                 270

Asn Pro Thr Val Thr Tyr Gly Lys Asn Gln Val Ile Met Leu Leu Tyr
        275                 280                 285

Pro Asp His Pro Thr Leu Leu Ser Tyr Arg Asn Met Gly Glu Glu Pro
    290                 295                 300

Asn Tyr Gln Glu Glu Trp Val Met His Lys Lys Glu Val Val Leu Thr
305                 310                 315                 320

Val Pro Thr Glu Gly Leu Glu Val Thr Trp Gly Asn Asn Glu Pro Tyr
                325                 330                 335

Lys Tyr Trp Pro Gln Leu Ser Thr Asn Gly Thr Ala His Gly His Pro
            340                 345                 350

His Glu Ile Ile Leu Tyr Tyr Tyr Glu Leu Tyr Pro Thr Met Thr Val
        355                 360                 365

Val Val Val Ser Val Ala Thr Phe Ile Leu Leu Ser Met Val Gly Met
    370                 375                 380

Ala Ala Gly Met Cys Met Cys Ala Arg Arg Arg Cys Ile Thr Pro Tyr
385                 390                 395                 400

Glu Leu Thr Pro Gly Ala Thr Val Pro Phe Leu Leu Ser Leu Ile Cys
```

<210> SEQ ID NO 12
<211> LENGTH: 261
<212> TYPE: PRT
<213> ORGANISM: Artificial Sequence
<220> FEATURE:
<223> OTHER INFORMATION: CHIKV capsid consensus

<400> SEQUENCE: 12

```
Met Glu Phe Ile Pro Thr Gln Thr Phe Tyr Asn Arg Arg Tyr Gln Pro
1               5                   10                  15
Arg Pro Trp Thr Pro Arg Pro Thr Ile Gln Val Ile Arg Pro Arg Pro
            20                  25                  30
Arg Pro Gln Arg Gln Ala Gly Gln Leu Ala Gln Leu Ile Ser Ala Val
        35                  40                  45
Asn Lys Leu Thr Met Arg Ala Val Pro Gln Gln Lys Pro Arg Arg Asn
    50                  55                  60
Arg Lys Asn Lys Lys Gln Lys Gln Gln Ala Pro Gln Asn Asn
65                  70                  75                  80
Thr Asn Gln Lys Lys Gln Pro Pro Lys Lys Pro Ala Gln Lys Lys
                85                  90                  95
Lys Lys Pro Gly Arg Arg Glu Arg Met Cys Met Lys Ile Glu Asn Asp
            100                 105                 110
Cys Ile Phe Glu Val Lys His Glu Gly Lys Val Thr Gly Tyr Ala Cys
        115                 120                 125
Leu Val Gly Asp Lys Val Met Lys Pro Ala His Val Lys Gly Thr Ile
    130                 135                 140
Asp Asn Ala Asp Leu Ala Lys Leu Ala Phe Lys Arg Ser Ser Lys Tyr
145                 150                 155                 160
Asp Leu Glu Cys Ala Gln Ile Pro Val His Met Lys Ser Asp Ala Ser
                165                 170                 175
Lys Phe Thr His Glu Lys Pro Glu Gly Tyr Tyr Asn Trp His His Gly
            180                 185                 190
Ala Val Gln Tyr Ser Gly Gly Arg Phe Thr Ile Pro Thr Gly Ala Gly
        195                 200                 205
Lys Pro Gly Asp Ser Gly Arg Pro Ile Phe Asp Asn Lys Gly Arg Val
    210                 215                 220
Val Ala Ile Val Leu Gly Gly Ala Asn Glu Gly Ala Arg Thr Ala Leu
225                 230                 235                 240
Ser Val Val Thr Trp Asn Lys Asp Ile Val Thr Lys Ile Thr Pro Glu
                245                 250                 255
Gly Ala Glu Glu Trp
            260
```

<210> SEQ ID NO 13
<211> LENGTH: 3008
<212> TYPE: DNA
<213> ORGANISM: Artificial Sequence
<220> FEATURE:
<223> OTHER INFORMATION: CHIKV Env consensus

<400> SEQUENCE: 13

```
atggactgga cctggatcct gttcctggtg gctgctgcca cccgcgtgca cagcagcctg    60
gccatccccg tgatgtgcct gctggccaac accaccttcc cttgcagcca gccccccctgc  120
```

```
accccctgct gctacgagaa agagcccgag gaaaccctgc ggatgctgga agataacgtg    180
atgaggcccg gctactacca gctgctccag gccagcctga cctgctcccc ccaccggcag    240
cggcggcgcg ggcgcaaacg ccgctctgcc accatggact ggacctggat cctgttcctg    300
gtcgctgctg ccacaagagt gcacagcagc accaaggaca acttcaacgt gtacaaggcc    360
acccggccct acctggccca ctgccccgat gcggcgagg ccacagctg ccacagcccc    420 gtggccctgg aacggatccg gaacgaggcc accgacggca ccctgaagat ccaggtgtcc    480
ctgcagatcg gcatcaagac cgacgacagc cacgactgga ccaagctgcg gtacatggac    540
aaccacatgc ccgccgacgc cgagagagcc ggcctgttcg tccggaccag cgcccctgc    600 accatcaccg gcaccatggg ccacttcatc ctggcccggt gcccaaggg cgagacactg    660 accgtgggct tcaccgacag ccggaagatc agccactcct gcacccaccc cttccaccac    720
gacccccccg tgatcggccg ggagaagttc cacagcaggc cccagcacgg caaagagctg    780
ccctgcagca cctacgtgca gagcaccgcc gccacaaccg aggaaatcga ggtgcacatg    840 cccccgata ccccgaccg gaccctgatg agccagcaga gcggcaacgt gaagatcacc    900
gtgaacggcc agaccgtgcg gtacaagtgc aactgcggcg gcagcaacga gggcctgacc    960
accaccgaca aggtgatcaa caactgcaag gtggaccagt gccacgccgc cgtgaccaac   1020
cacaagaagt ggcagtacaa cagcccctg gtgccccgga atgccgagct gggcgaccgg   1080
aagggcaaga tccacatccc cttcccctg gccaacgtga cctgccgggt gcccaaggcc   1140
cggaacccca ccgtgaccta cggcaagaac caggtgatca tgctgctgta ccccgaccac   1200
cccaccctgc tgtcctaccg gaacatgggc gaggaaccca actaccaaga ggagtgggtc   1260
atgcacaaga aagaagtggt gctgaccgtc ccaccgagg gcctggaagt gacctgggc   1320 aacaacgagc cctacaagta ctggccccag ctgtccacca cggcaccgc cacggccac   1380 ccccacgaga tcatcctgta ctactacgag ctgtacccta ccatgaccgt ggtggtggtg   1440
tccgtggcca cctttatcct gctgtccatg gtcggcatgg ccgctggcat gtgcatgtgc   1500
gccaggaggc gctgtatcac cccctacgag ctgacctg gcgccaccgt gccctttctg   1560
ctgtccctga tctgctgcat ccggaccgcc aaggcccgcg gcgcaaacg ccgctctgcc   1620 accatggact ggacctggat cctgtttctg gtcgctgctg ccaccgggt gcacagctac   1680 gagcacgtga ccgtgatccc caacaccgtg ggcgtgccct acaagaccct ggtgaacagg   1740
cccggctaca gccccatggt gctggaaatg gaactgctgt ccgtgaccct ggaacccacc   1800
ctgagcctgg actacatcac ctgcgagtac aagacagtga tccccagccc ctacgtgaag   1860
tgctgcggca ccgccgagtg caaggacaag aacctgcccg actacagctg caaggtgttc   1920
accggcgtgt accccttcat gtggggcgga gcctactgct tctgcgacgc cgagaacacc   1980
cagctgtccg aggcccacgt ggagaagagc gagagctgca gaccgagtt cgccagcgcc   2040 taccgggccc acacagccag cgccagcgcc aagctgcggg tgctgtacca gggcaacaac   2100
atcaccgtga ccgcctacgc caacggcgac cacgccgtga cagtgaagga cgccaagttc   2160
atcgtgggcc ccatgagcag cgcctggacc cccttcgaca caagatcgt ggtgtacaag   2220 ggcgacgtgt acaacatgga ctaccccccc ttcggagccg gcagacccgg ccagttcggc   2280
gacatccaga gccggacccc cgagagcaag gacgtgtacg ccaatcccca gctggtgctg   2340
cagagacccg ccgtgggcac cgtgcacgtg ccttacagcc aggccccag cggcttcaag   2400 tactggctga aagagagggg cgccagcctg cagcacaccc ccccttcgg ctgccagatc   2460
```

-continued

```
gccaccaacc ccgtgcgggc cgtgaattgt gccgtgggca acatgcccat cagcatcgac   2520
atccccgagg ccgccttcac cagggtggtg gacgcccccca gcctgaccga catgagctgc   2580
gaggtgcccg cctgcaccca cagcagcgac ttcggcggcg tggccatcat caagtacgcc   2640
gccagcaaga aaggcaagtg cgccgtgcac agcatgacca atgccgtgac catccgggag   2700
gccgagatcg aggtggaggg caacagccag ctgcagatca gcttcagcac cgccctggcc   2760
agcgccgagt tccgggtgca ggtctgcagc acccaggtgc actgtgccgc cgagtgtcac   2820
ccccccaagg accacatcgt gaactacccc gccagccaca ccaccctggg cgtgcaggac   2880
atcagcgcca ccgccatgag ctgggtgcag aagatcacag gcggcgtcgg cctggtggtg   2940
gccgtggccg ccctgatcct gatcgtggtg ctgtgcgtga gcttcagccg gcactgatga   3000
gcggccgc                                                              3008

<210> SEQ ID NO 14
<211> LENGTH: 998
<212> TYPE: PRT
<213> ORGANISM: Artificial Sequence
<220> FEATURE:
<223> OTHER INFORMATION: CHIKV Env consensus

<400> SEQUENCE: 14

Met Asp Trp Thr Trp Ile Leu Phe Leu Val Ala Ala Ala Thr Arg Val
1               5                   10                  15

His Ser Ser Leu Ala Ile Pro Val Met Cys Leu Leu Ala Asn Thr Thr
            20                  25                  30

Phe Pro Cys Ser Gln Pro Pro Cys Thr Pro Cys Cys Tyr Glu Lys Glu
        35                  40                  45

Pro Glu Glu Thr Leu Arg Met Leu Glu Asp Asn Val Met Arg Pro Gly
    50                  55                  60

Tyr Tyr Gln Leu Leu Gln Ala Ser Leu Thr Cys Ser Pro His Arg Gln
65                  70                  75                  80

Arg Arg Arg Gly Arg Lys Arg Arg Ser Ala Thr Met Asp Trp Thr Trp
                85                  90                  95

Ile Leu Phe Leu Val Ala Ala Ala Thr Arg Val His Ser Ser Thr Lys
            100                 105                 110

Asp Asn Phe Asn Val Tyr Lys Ala Thr Arg Pro Tyr Leu Ala His Cys
        115                 120                 125

Pro Asp Cys Gly Glu Gly His Ser Cys His Ser Pro Val Ala Leu Glu
    130                 135                 140

Arg Ile Arg Asn Glu Ala Thr Asp Gly Thr Leu Lys Ile Gln Val Ser
145                 150                 155                 160

Leu Gln Ile Gly Ile Lys Thr Asp Asp Ser His Asp Trp Thr Lys Leu
                165                 170                 175

Arg Tyr Met Asp Asn His Met Pro Ala Asp Ala Glu Arg Ala Gly Leu
            180                 185                 190

Phe Val Arg Thr Ser Ala Pro Cys Thr Ile Thr Gly Thr Met Gly His
        195                 200                 205

Phe Ile Leu Ala Arg Cys Pro Lys Gly Glu Thr Leu Thr Val Gly Phe
    210                 215                 220

Thr Asp Ser Arg Lys Ile Ser His Ser Cys Thr His Pro Phe His His
225                 230                 235                 240

Asp Pro Pro Val Ile Gly Arg Glu Lys Phe His Ser Arg Pro Gln His
                245                 250                 255

Gly Lys Glu Leu Pro Cys Ser Thr Tyr Val Gln Ser Thr Ala Ala Thr
```

```
                    260                 265                 270
        Thr Glu Glu Ile Glu Val His Met Pro Pro Asp Thr Pro Asp Arg Thr
                    275                 280                 285

Leu Met Ser Gln Gln Ser Gly Asn Val Lys Ile Thr Val Asn Gly Gln
                    290                 295                 300

Thr Val Arg Tyr Lys Cys Asn Cys Gly Gly Ser Asn Glu Gly Leu Thr
        305                 310                 315                 320

Thr Thr Asp Lys Val Ile Asn Asn Cys Lys Val Asp Gln Cys His Ala
                        325                 330                 335

Ala Val Thr Asn His Lys Lys Trp Gln Tyr Asn Ser Pro Leu Val Pro
                        340                 345                 350

Arg Asn Ala Glu Leu Gly Asp Arg Lys Gly Lys Ile His Ile Pro Phe
                        355                 360                 365

Pro Leu Ala Asn Val Thr Cys Arg Val Pro Lys Ala Arg Asn Pro Thr
                        370                 375                 380

Val Thr Tyr Gly Lys Asn Gln Val Ile Met Leu Leu Tyr Pro Asp His
        385                 390                 395                 400

Pro Thr Leu Leu Ser Tyr Arg Asn Met Gly Glu Glu Pro Asn Tyr Gln
                        405                 410                 415

Glu Glu Trp Val Met His Lys Lys Glu Val Val Leu Thr Val Pro Thr
                        420                 425                 430

Glu Gly Leu Glu Val Thr Trp Gly Asn Asn Glu Pro Tyr Lys Tyr Trp
                        435                 440                 445

Pro Gln Leu Ser Thr Asn Gly Thr Ala His Gly His Pro His Glu Ile
                        450                 455                 460

Ile Leu Tyr Tyr Tyr Glu Leu Tyr Pro Thr Met Thr Val Val Val Val
        465                 470                 475                 480

Ser Val Ala Thr Phe Ile Leu Leu Ser Met Val Gly Met Ala Ala Gly
                        485                 490                 495

Met Cys Met Cys Ala Arg Arg Arg Cys Ile Thr Pro Tyr Glu Leu Thr
                        500                 505                 510

Pro Gly Ala Thr Val Pro Phe Leu Leu Ser Leu Ile Cys Cys Ile Arg
                        515                 520                 525

Thr Ala Lys Ala Arg Gly Arg Lys Arg Ser Ala Thr Met Asp Trp
                        530                 535                 540

Thr Trp Ile Leu Phe Leu Val Ala Ala Thr Arg Val His Ser Tyr
        545                 550                 555                 560

Glu His Val Thr Val Ile Pro Asn Thr Val Gly Val Pro Tyr Lys Thr
                        565                 570                 575

Leu Val Asn Arg Pro Gly Tyr Ser Pro Met Val Leu Glu Met Glu Leu
                        580                 585                 590

Leu Ser Val Thr Leu Glu Pro Thr Leu Ser Leu Asp Tyr Ile Thr Cys
                        595                 600                 605

Glu Tyr Lys Thr Val Ile Pro Ser Pro Tyr Val Lys Cys Cys Gly Thr
                        610                 615                 620

Ala Glu Cys Lys Asp Lys Asn Leu Pro Asp Tyr Ser Cys Lys Val Phe
        625                 630                 635                 640

Thr Gly Val Tyr Pro Phe Met Trp Gly Gly Ala Tyr Cys Phe Cys Asp
                        645                 650                 655

Ala Glu Asn Thr Gln Leu Ser Glu Ala His Val Glu Lys Ser Glu Ser
                        660                 665                 670

Cys Lys Thr Glu Phe Ala Ser Ala Tyr Arg Ala His Thr Ala Ser Ala
                        675                 680                 685
```

```
Ser Ala Lys Leu Arg Val Leu Tyr Gln Gly Asn Asn Ile Thr Val Thr
    690                 695                 700

Ala Tyr Ala Asn Gly Asp His Ala Val Thr Val Lys Asp Ala Lys Phe
705                 710                 715                 720
Ile Val Gly Pro Met Ser Ser Ala Trp Thr Pro Phe Asp Asn Lys Ile
                725                 730                 735
Val Val Tyr Lys Gly Asp Val Tyr Asn Met Asp Tyr Pro Pro Phe Gly
            740                 745                 750
Ala Gly Arg Pro Gly Gln Phe Gly Asp Ile Gln Ser Arg Thr Pro Glu
        755                 760                 765
Ser Lys Asp Val Tyr Ala Asn Thr Gln Leu Val Leu Gln Arg Pro Ala
    770                 775                 780

Val Gly Thr Val His Val Pro Tyr Ser Gln Ala Pro Ser Gly Phe Lys
785                 790                 795                 800
Tyr Trp Leu Lys Glu Arg Gly Ala Ser Leu Gln His Thr Ala Pro Phe
                805                 810                 815
Gly Cys Gln Ile Ala Thr Asn Pro Val Arg Ala Val Asn Cys Ala Val
            820                 825                 830
Gly Asn Met Pro Ile Ser Ile Asp Ile Pro Glu Ala Ala Phe Thr Arg
        835                 840                 845
Val Val Asp Ala Pro Ser Leu Thr Asp Met Ser Cys Glu Val Pro Ala
    850                 855                 860

Cys Thr His Ser Ser Asp Phe Gly Gly Val Ala Ile Ile Lys Tyr Ala
865                 870                 875                 880
Ala Ser Lys Lys Gly Lys Cys Ala Val His Ser Met Thr Asn Ala Val
                885                 890                 895
Thr Ile Arg Glu Ala Glu Ile Glu Val Glu Gly Asn Ser Gln Leu Gln
            900                 905                 910
Ile Ser Phe Ser Thr Ala Leu Ala Ser Ala Glu Phe Arg Val Gln Val
        915                 920                 925
Cys Ser Thr Gln Val His Cys Ala Ala Glu Cys His Pro Pro Lys Asp
    930                 935                 940

His Ile Val Asn Tyr Pro Ala Ser His Thr Thr Leu Gly Val Gln Asp
945                 950                 955                 960
Ile Ser Ala Thr Ala Met Ser Trp Val Gln Lys Ile Thr Gly Gly Val
                965                 970                 975
Gly Leu Val Val Ala Val Ala Ala Leu Ile Leu Ile Val Val Leu Cys
            980                 985                 990
Val Ser Phe Ser Arg His
        995
```

<210> SEQ ID NO 15
<211> LENGTH: 2954
<212> TYPE: DNA
<213> ORGANISM: Artificial Sequence
<220> FEATURE:
<223> OTHER INFORMATION: CHIKV Env consensus

<400> SEQUENCE: 15

```
agcctggcca tccccgtgat gtgcctgctg gccaacacca ccttcccttg cagccagccc      60
ccctgcaccc cctgctgcta cgagaaagag cccgaggaaa ccctgcggat gctggaagat     120
aacgtgatga ggcccggcta ctaccagctg ctccaggcca gcctgacctg ctcccccac      180 cggcagcggc ggcgcgggcg caaacgccgc tctgccacca tggactggac ctggatcctg     240
```

```
ttcctggtcg ctgctgccac aagagtgcac agcagcacca aggacaactt caacgtgtac    300
aaggccaccc ggccctacct ggcccactgc cccgattgcg gcgagggcca cagctgccac    360
agccccgtgg ccctggaacg gatccggaac gaggccaccg acggcaccct gaagatccag    420
gtgtccctgc agatcggcat caagaccgac gacagccacg actggaccaa gctgcggtac    480
atggacaacc acatgcccgc cgacgccgag agagccggcc tgttcgtccg gaccagcgcc    540
ccctgcacca tcaccggcac catgggccac ttcatcctgg cccggtgccc caagggcgag    600
acactgaccg tgggcttcac cgacagccgg aagatcagcc actcctgcac ccacccttc     660 caccacgacc cccccgtgat cggcggggag aagttccaca gcaggcccca gcacggcaaa    720
gagctgccct gcagcaccta cgtgcagagc accgccgcca caaccgagga aatcgaggtg    780
cacatgcccc ccgatacccc cgaccggacc ctgatgagcc agcagagcgg caacgtgaag    840
atcaccgtga acgccagac cgtgcggtac aagtgcaact gcggcggcag caacgagggc    900
ctgaccacca ccgacaaggt gatcaacaac tgcaaggtgg accagtgcca cgccgccgtg    960
accaaccaca agaagtggca gtacaacagc cccctggtgc cccggaatgc cgagctgggc   1020
gaccggaagg gcaagatcca catccccttc cccctggcca acgtgacctg ccgggtgccc   1080
aaggcccgga accccaccgt gacctacggc aagaaccagg tgatcatgct gctgtacccc   1140
gaccacccca ccctgctgtc ctaccggaac atgggcgagg aacccaacta ccaagaggag   1200
tgggtcatgc acaagaaaga agtggtgctg accgtcccca ccgagggcct ggaagtgacc   1260
tggggcaaca cgagcccta caagtactgg ccccagctgt ccaccaacgg caccgcccac   1320
ggccacccca cgagatcat cctgtactac tacgagctgt accctaccat gaccgtggtg   1380
gtggtgtccg tggccacctt tatcctgctg tccatggtcg gcatggccgc tggcatgtgc   1440
atgtgcgcca ggaggcgctg tatcacccc tacgagctga cacctggcgc caccgtgccc   1500
tttctgctgt ccctgatctg ctgcatccgg accgccaagg cccgcgggcg caaacgccgc   1560
tctgccacca tggactggac ctggatcctg tttctggtcg ctgctgccac ccgggtgcac   1620
agctacgagc acgtgaccgt gatccccaac accgtgggcg tgccctacaa gaccctggtg   1680
aacaggcccg gctacagccc catggtgctg gaaatggaac tgctgtccgt gaccctggaa   1740
cccaccctga gcctggacta catcacctgc gagtacaaga cagtgatccc cagcccctac   1800
gtgaagtgct gcggcaccgc cgagtgcaag gacaagaacc tgcccgacta cagctgcaag   1860
gtgttcaccg gcgtgtaccc cttcatgtgg ggcggagcct actgcttctg cgacgccgag   1920
aacacccagc tgtccgaggc ccacgtggag aagagcgaga gctgcaagac cgagttcgcc   1980
agcgcctacc gggcccacac agccagcgcc agcgccaagc tgcgggtgct gtaccagggc   2040
aacaacatca ccgtgaccgc ctacgccaac ggcgaccacg ccgtgacagt gaaggacgcc   2100
aagttcatcg tgggccccat gagcagcgcc tggacccctc tcgacaacaa gatcgtggtg   2160
tacaagggcg acgtgtacaa catggactac ccccccttcg agccggcag acccggccag   2220 ttcggcgaca tccagagccg gacccccgag agcaaggacg tgtacgccaa tacccagctg   2280
gtgctgcaga gaccgccgt gggcaccgtg cacgtgcctt acagccaggc ccccagcggc   2340
ttcaagtact ggctgaaaga gagggcgcc agcctgcagc acaccgcccc cttcggctgc   2400
cagatcgcca ccaaccccgt gcgggccgtg aattgtgccg tgggcaacat gcccatcagc   2460
atcgacatcc ccgaggccgc cttcaccagg gtggtggacg ccccagcct gaccgacatg   2520 agctgcgagg tgcccgcctg cacccacagc agcgacttcg gcggcgtggc catcatcaag   2580
tacgccgcca gcaagaaagg caagtgcgcc gtgcacagca tgaccaatgc cgtgaccatc   2640
```

-continued

```
cgggaggccg agatcgaggt ggagggcaac agccagctgc agatcagctt cagcaccgcc    2700
ctggccagcg ccgagttccg ggtgcaggtc tgcagcaccc aggtgcactg tgccgccgag    2760
tgtcaccccc ccaaggacca catcgtgaac taccccgcca gccacaccac cctgggcgtg    2820
caggacatca gcgccaccgc catgagctgg gtgcagaaga tcacaggcgg cgtcggcctg    2880
gtggtggccg tggccgccct gatcctgatc gtggtgctgt gcgtgagctt cagccggcac    2940
tgatgagcgg ccgc                                                      2954
```

<210> SEQ ID NO 16
<211> LENGTH: 980
<212> TYPE: PRT
<213> ORGANISM: Artificial Sequence
<220> FEATURE:
<223> OTHER INFORMATION: CHIKV Env consensus

<400> SEQUENCE: 16

```
Ser Leu Ala Ile Pro Val Met Cys Leu Leu Ala Asn Thr Thr Phe Pro
1               5                   10                  15

Cys Ser Gln Pro Pro Cys Thr Pro Cys Cys Tyr Glu Lys Glu Pro Glu
            20                  25                  30

Glu Thr Leu Arg Met Leu Glu Asp Asn Val Met Arg Pro Gly Tyr Tyr
        35                  40                  45

Gln Leu Leu Gln Ala Ser Leu Thr Cys Ser Pro His Arg Gln Arg Arg
    50                  55                  60

Arg Gly Arg Lys Arg Ser Ala Thr Met Asp Trp Thr Trp Ile Leu
65                  70                  75                  80

Phe Leu Val Ala Ala Thr Arg Val His Ser Ser Thr Lys Asp Asn
                85                  90                  95

Phe Asn Val Tyr Lys Ala Thr Arg Pro Tyr Leu Ala His Cys Pro Asp
            100                 105                 110

Cys Gly Glu Gly His Ser Cys His Ser Pro Val Ala Leu Glu Arg Ile
        115                 120                 125

Arg Asn Glu Ala Thr Asp Gly Thr Leu Lys Ile Gln Val Ser Leu Gln
    130                 135                 140

Ile Gly Ile Lys Thr Asp Asp Ser His Asp Trp Thr Lys Leu Arg Tyr
145                 150                 155                 160

Met Asp Asn His Met Pro Ala Asp Ala Glu Arg Ala Gly Leu Phe Val
                165                 170                 175

Arg Thr Ser Ala Pro Cys Thr Ile Thr Gly Thr Met Gly His Phe Ile
            180                 185                 190

Leu Ala Arg Cys Pro Lys Gly Glu Thr Leu Thr Val Gly Phe Thr Asp
        195                 200                 205

Ser Arg Lys Ile Ser His Ser Cys Thr His Pro Phe His His Asp Pro
    210                 215                 220

Pro Val Ile Gly Arg Glu Lys Phe His Ser Arg Pro Gln His Gly Lys
225                 230                 235                 240

Glu Leu Pro Cys Ser Thr Tyr Val Gln Ser Thr Ala Ala Thr Thr Glu
                245                 250                 255

Glu Ile Glu Val His Met Pro Pro Asp Thr Pro Asp Arg Thr Leu Met
            260                 265                 270

Ser Gln Gln Ser Gly Asn Val Lys Ile Thr Val Asn Gly Gln Thr Val
        275                 280                 285

Arg Tyr Lys Cys Asn Cys Gly Gly Ser Asn Glu Gly Leu Thr Thr Thr
    290                 295                 300
```

```
Asp Lys Val Ile Asn Asn Cys Lys Val Asp Gln Cys His Ala Ala Val
305                 310                 315                 320

Thr Asn His Lys Lys Trp Gln Tyr Asn Ser Pro Leu Val Pro Arg Asn
            325                 330                 335

Ala Glu Leu Gly Asp Arg Lys Gly Lys Ile His Ile Pro Phe Pro Leu
            340                 345                 350

Ala Asn Val Thr Cys Arg Val Pro Lys Ala Arg Asn Pro Thr Val Thr
            355                 360                 365

Tyr Gly Lys Asn Gln Val Ile Met Leu Leu Tyr Pro Asp His Pro Thr
        370                 375                 380

Leu Leu Ser Tyr Arg Asn Met Gly Glu Glu Pro Asn Tyr Gln Glu Glu
385                 390                 395                 400

Trp Val Met His Lys Lys Glu Val Val Leu Thr Val Pro Thr Glu Gly
                405                 410                 415

Leu Glu Val Thr Trp Gly Asn Asn Glu Pro Tyr Lys Tyr Trp Pro Gln
            420                 425                 430

Leu Ser Thr Asn Gly Thr Ala His Gly His Pro His Glu Ile Ile Leu
        435                 440                 445

Tyr Tyr Tyr Glu Leu Tyr Pro Thr Met Thr Val Val Val Ser Val
450                 455                 460

Ala Thr Phe Ile Leu Leu Ser Met Val Gly Met Ala Ala Gly Met Cys
465                 470                 475                 480

Met Cys Ala Arg Arg Cys Ile Thr Pro Tyr Glu Leu Thr Pro Gly
            485                 490                 495

Ala Thr Val Pro Phe Leu Leu Ser Leu Ile Cys Cys Ile Arg Thr Ala
            500                 505                 510

Lys Ala Arg Gly Arg Lys Arg Ser Ala Thr Met Asp Trp Thr Trp
            515                 520                 525

Ile Leu Phe Leu Val Ala Ala Ala Thr Arg Val His Ser Tyr Glu His
        530                 535                 540

Val Thr Val Ile Pro Asn Thr Val Gly Val Pro Tyr Lys Thr Leu Val
545                 550                 555                 560

Asn Arg Pro Gly Tyr Ser Pro Met Val Leu Glu Met Glu Leu Leu Ser
                565                 570                 575

Val Thr Leu Glu Pro Thr Leu Ser Leu Asp Tyr Ile Thr Cys Glu Tyr
            580                 585                 590

Lys Thr Val Ile Pro Ser Pro Tyr Val Lys Cys Cys Gly Thr Ala Glu
        595                 600                 605

Cys Lys Asp Lys Asn Leu Pro Asp Tyr Ser Cys Lys Val Phe Thr Gly
        610                 615                 620

Val Tyr Pro Phe Met Trp Gly Gly Ala Tyr Cys Phe Cys Asp Ala Glu
625                 630                 635                 640

Asn Thr Gln Leu Ser Glu Ala His Val Glu Lys Ser Glu Ser Cys Lys
                645                 650                 655

Thr Glu Phe Ala Ser Ala Tyr Arg Ala His Thr Ala Ser Ala Ser Ala
                660                 665                 670

Lys Leu Arg Val Leu Tyr Gln Gly Asn Asn Ile Thr Val Thr Ala Tyr
            675                 680                 685

Ala Asn Gly Asp His Ala Val Thr Val Lys Asp Ala Lys Phe Ile Val
        690                 695                 700

Gly Pro Met Ser Ser Ala Trp Thr Pro Phe Asp Asn Lys Ile Val Val
705                 710                 715                 720
```

```
Tyr Lys Gly Asp Val Tyr Asn Met Asp Tyr Pro Pro Phe Gly Ala Gly
            725                 730                 735

Arg Pro Gly Gln Phe Gly Asp Ile Gln Ser Arg Thr Pro Glu Ser Lys
        740                 745                 750

Asp Val Tyr Ala Asn Thr Gln Leu Val Leu Gln Arg Pro Ala Val Gly
        755                 760                 765

Thr Val His Val Pro Tyr Ser Gln Ala Pro Ser Gly Phe Lys Tyr Trp
        770                 775                 780

Leu Lys Glu Arg Gly Ala Ser Leu Gln His Thr Ala Pro Phe Gly Cys
785                 790                 795                 800

Gln Ile Ala Thr Asn Pro Val Arg Ala Val Asn Cys Ala Val Gly Asn
            805                 810                 815

Met Pro Ile Ser Ile Asp Ile Pro Glu Ala Ala Phe Thr Arg Val Val
            820                 825                 830

Asp Ala Pro Ser Leu Thr Asp Met Ser Cys Glu Val Pro Ala Cys Thr
        835                 840                 845

His Ser Ser Asp Phe Gly Gly Val Ala Ile Ile Lys Tyr Ala Ala Ser
        850                 855                 860

Lys Lys Gly Lys Cys Ala Val His Ser Met Thr Asn Ala Val Thr Ile
865                 870                 875                 880

Arg Glu Ala Glu Ile Glu Val Glu Gly Asn Ser Gln Leu Gln Ile Ser
                885                 890                 895

Phe Ser Thr Ala Leu Ala Ser Ala Glu Phe Arg Val Gln Val Cys Ser
            900                 905                 910

Thr Gln Val His Cys Ala Ala Glu Cys His Pro Pro Lys Asp His Ile
        915                 920                 925

Val Asn Tyr Pro Ala Ser His Thr Thr Leu Gly Val Gln Asp Ile Ser
        930                 935                 940

Ala Thr Ala Met Ser Trp Val Gln Lys Ile Thr Gly Gly Val Gly Leu
945                 950                 955                 960

Val Val Ala Val Ala Ala Leu Ile Leu Ile Val Val Leu Cys Val Ser
                965                 970                 975

Phe Ser Arg His
            980

<210> SEQ ID NO 17
<211> LENGTH: 18
<212> TYPE: PRT
<213> ORGANISM: Homo sapiens

<400> SEQUENCE: 17

Met Asp Trp Thr Trp Ile Leu Phe Leu Val Ala Ala Ala Thr Arg Val
1               5                   10                  15

His Ser

<210> SEQ ID NO 18
<211> LENGTH: 9
<212> TYPE: PRT
<213> ORGANISM: Artificial Sequence
<220> FEATURE:
<223> OTHER INFORMATION: E1 dominant epitope

<400> SEQUENCE: 18

His Ser Met Thr Asn Ala Val Thr Ile
1               5

<210> SEQ ID NO 19
```

```
<211> LENGTH: 9
<212> TYPE: PRT
<213> ORGANISM: Artificial Sequence
<220> FEATURE:
<223> OTHER INFORMATION: E2 dominant epitope

<400> SEQUENCE: 19

Ile Ile Leu Tyr Tyr Tyr Glu Leu Tyr
1               5

<210> SEQ ID NO 20
<211> LENGTH: 9
<212> TYPE: PRT
<213> ORGANISM: Artificial Sequence
<220> FEATURE:
<223> OTHER INFORMATION: ACLVGDKVM

<400> SEQUENCE: 20

Ala Cys Leu Val Gly Asp Lys Val Met
1               5
```